(12) United States Patent
Medoff

(10) Patent No.: US 9,321,850 B2
(45) Date of Patent: Apr. 26, 2016

(54) PROCESSING BIOMASS

(71) Applicant: XYLECO, INC., Woburn, MA (US)

(72) Inventor: Marshall Medoff, Brookline, MA (US)

(73) Assignee: XYLECO, INC., Wakefield, MA (US)

(*) Notice: Subject to any disclaimer, the term of this patent is extended or adjusted under 35 U.S.C. 154(b) by 0 days.

(21) Appl. No.: 14/579,926

(22) Filed: Dec. 22, 2014

(65) Prior Publication Data

US 2015/0108693 A1 Apr. 23, 2015

Related U.S. Application Data

(63) Continuation of application No. 13/099,151, filed on May 2, 2011, now Pat. No. 8,945,352, which is a continuation of application No. PCT/US2009/064307, filed on Nov. 13, 2009.

(60) Provisional application No. 61/115,398, filed on Nov. 17, 2008.

(51) Int. Cl.
| C08B 1/00 | (2006.01) |
|---|---|
| C12P 7/08 | (2006.01) |
| C10L 5/44 | (2006.01) |
| C12P 7/10 | (2006.01) |
| B01J 19/08 | (2006.01) |
| C08H 8/00 | (2010.01) |

(52) U.S. Cl.
CPC ............... *C08B 1/00* (2013.01); *B01J 19/085* (2013.01); *C10L 5/44* (2013.01); *C12P 7/08* (2013.01); *C12P 7/10* (2013.01); *B01J 2219/0879* (2013.01); *C08H 8/00* (2013.01); *C12P 2201/00* (2013.01); *Y02E 50/10* (2013.01); *Y02E 50/16* (2013.01); *Y02E 50/30* (2013.01); *Y02E 50/343* (2013.01)

(58) Field of Classification Search
None
See application file for complete search history.

(56) References Cited

U.S. PATENT DOCUMENTS

| 4,088,528 | A | 5/1978 | Berger et al. |
|---|---|---|---|
| 4,295,048 | A | 10/1981 | Cleland et al. |
| 4,316,748 | A | 2/1982 | Rugg et al. |
| 4,363,671 | A | 12/1982 | Rugg et al. |
| 4,368,079 | A | 1/1983 | Rugg et al. |
| 4,633,611 | A | 1/1987 | Schiller et al. |
| 4,738,087 | A | 4/1988 | Lundahl |
| 4,859,853 | A | 8/1989 | Kronenberg |
| 5,916,780 | A | 6/1999 | Foody et al. |
| 5,916,929 | A | 6/1999 | Knobel et al. |
| 6,620,292 | B2 | 9/2003 | Wingerson |
| 7,600,707 | B2 | 10/2009 | Wingerson |
| 2003/0009151 | A1* | 1/2003 | Wang ............... A61M 25/0009 604/526 |
| 2004/0072699 | A1 | 4/2004 | Liu et al. |
| 2006/0141584 | A1* | 6/2006 | Litzen .................. C12P 7/06 435/105 |
| 2006/0143977 | A1 | 7/2006 | Meijer et al. |

FOREIGN PATENT DOCUMENTS

| CA | 2823380 | 6/2008 |
|---|---|---|
| JP | 07-080437 | 3/1995 |
| JP | 11101900 | 4/1999 |
| JP | 2003129058 | 5/2003 |
| RU | 2239329 | 11/2004 |
| WO | 2006024242 | 3/2006 |
| WO | 2008073186 | 6/2008 |
| WO | 2009134791 | 11/2009 |
| WO | 2009134816 | 11/2009 |

OTHER PUBLICATIONS

Ziaie, F et al. Investigation of beam uniformity in industrial electron accelerator. Radiation Measurements. 2001. 34: 609-613.*
Eurasian Search Report, Eurasian Application No. 201401308, dated Apr. 28, 2015, 2 pages.
Daigle D.J. et al., "Solidstate Fementation Plus Extrusion to Make Biopesticide Granules", Biotechnology Techniques, vol. 12, No. 10, Oct. 1998, pp. 715-719.
Ho, K.G. et al., "Ingredient Selection for Plastic Composite Supports for L-(1)-Lactic Acid Biofilm Fermentation by *Lactobacillus casei* Subsp. *rhamnosus*", Applied and Environmental Microbiology, vol. 63, No. 7, Jul. 1997, pp. 2516-2523.
Linko P. et al., "Extrusion Cooking of Barley Starch for the Production of Glucose Syrup and Ethanol", Journal of Cereal Science, vol. 1, Issue 4, Oct. 1983, pp. 275-284.
Kumakura, M. et al., "Radiation-Induced Decomposition and Enzymatic Hydrolysis of Cellulose", Biotechnology and Bioengineering, vol. 20, No. 8, 1978, pp. 1309-1315.
ISR for International Application No. PCT/US2009/064307, mailed May 28, 2010, 2 pages.
IPRP for International Application No. PCT/US2009/064307, mailed May 26, 2011, 5 pages.
Driscoll, M. et al., "Electron Beam Irradiation of Cellulose", Radiation Physics and Chemistry, vol. 78, Jul.-Aug. 2009, pp. 539-542.
Eurasian Office Action—Corresponding Application No. 201170701—dated Mar. 1, 2013, 1 page.

* cited by examiner

*Primary Examiner* — Renee Clayton
*Assistant Examiner* — Susan E Fernandez
(74) *Attorney, Agent, or Firm* — Leber Patent Law P.C.

(57) ABSTRACT

Methods are provided for reducing one or more dimensions of individual pieces of biomass; treating biomass, such as size-reduced biomass; changing a molecular structure of a biomass material; and, optionally, subjecting the biomass to a primary process to form a product. The methods include processing biomass materials using a screw extrusion process, and treating the biomass material with a screw extrusion process in size-reduction and treating steps.

23 Claims, 15 Drawing Sheets

VACUUM SOURCE 252

(Prior Art Apparatus)

(Prior Art Apparatus)

(Prior Art Apparatus)

(Prior Art Apparatus)

(Prior Art Apparatus)

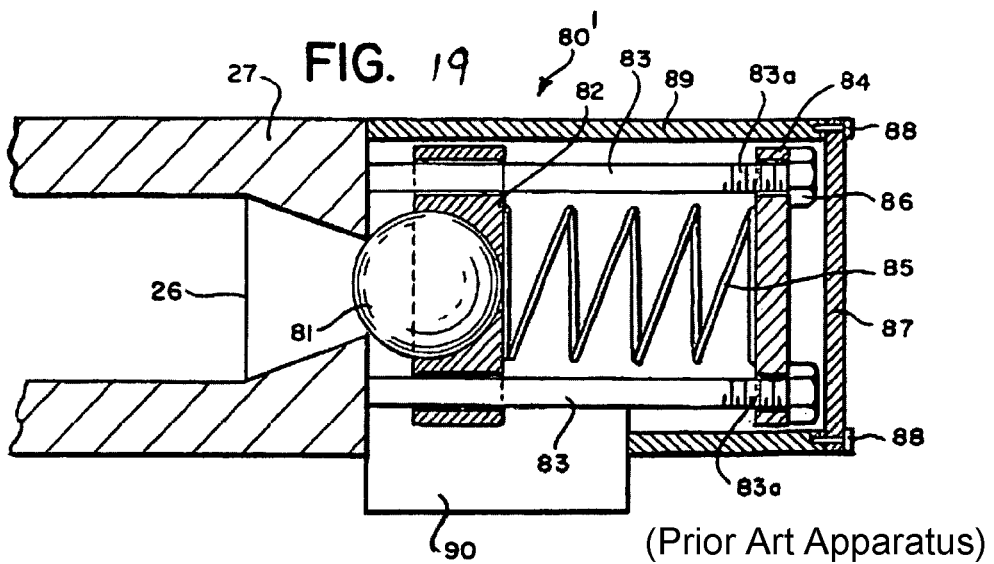
FIG. 19 (Prior Art Apparatus)
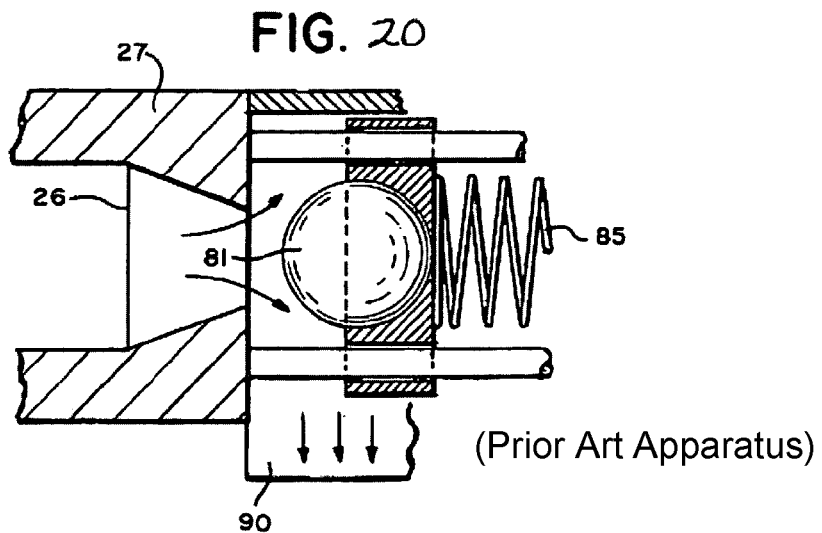
FIG. 20 (Prior Art Apparatus)
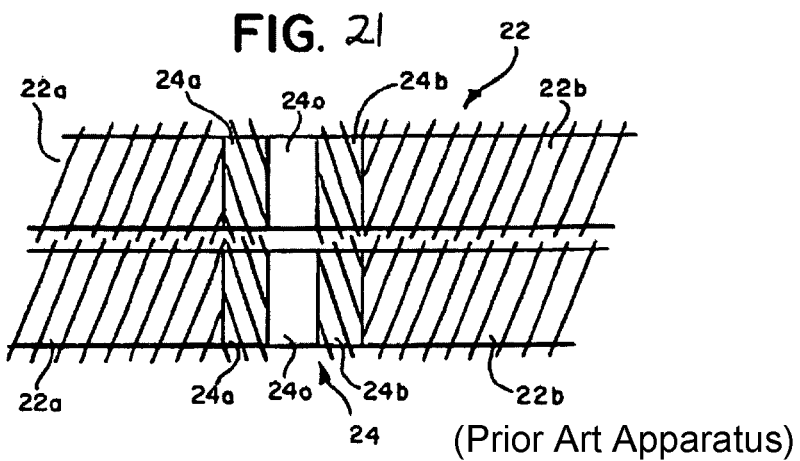
FIG. 21 (Prior Art Apparatus)

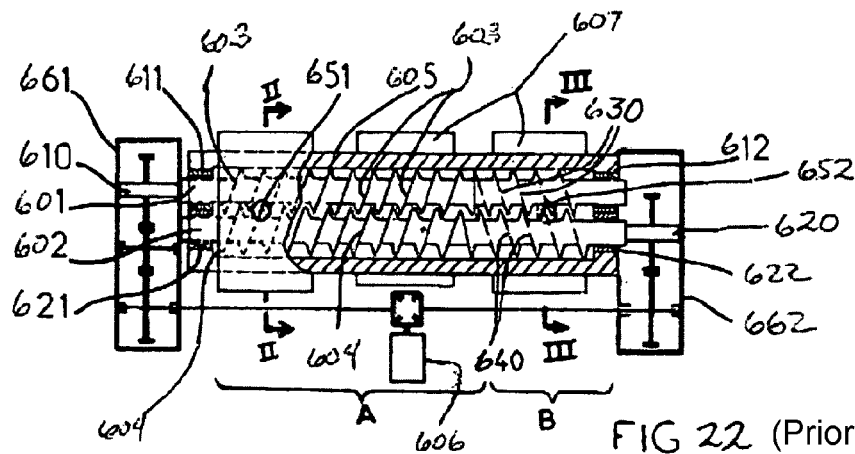
FIG 22 (Prior Art Apparatus)
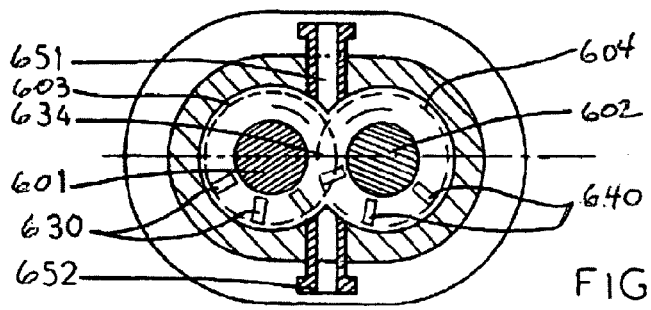
FIG 23 (Prior Art Apparatus)
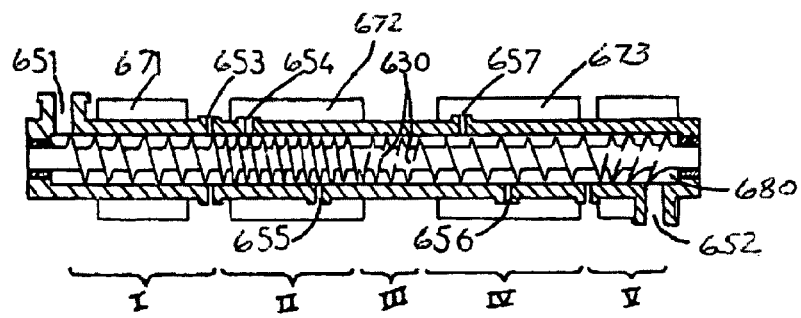
FIG 24 (Prior Art Apparatus)

PROCESSING BIOMASS

CROSS-REFERENCE TO RELATED APPLICATIONS

This application is a continuation of U.S. patent application Ser. No. 13/099,151, filed May 2, 2011, which is a continuation application of PCT Application Serial No. PCT/US2009/064307, filed Nov. 13, 2009, which claimed priority from U.S. Provisional Application Ser. No. 61/115,398, filed on Nov. 17, 2008. The entirety of each of these applications is incorporated herein by reference.

TECHNICAL FIELD

This invention relates to processing biomass, and products made therefrom.

BACKGROUND

Cellulosic and lignocellulosic materials, e.g., in fibrous form, are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Generally, this invention relates to carbohydrate-containing materials (e.g., biomass materials or biomass-derived materials), methods of making and processing such materials (e.g., to change their structure), and products made from the materials. For example, many of the methods described herein can provide cellulosic and/or lignocellulosic materials that have a lower recalcitrance level, a lower molecular weight and/or crystallinity relative to a native material. Many of the methods provide materials that react more rapidly, e.g., with an acid, base, or an enzyme, and/or that can be more readily utilized by a variety of microorganisms to produce useful products, such as hydrogen, alcohols (e.g., ethanol or butanol), organic acids (e.g., acetic acid), hydrocarbons, co-products (e.g., proteins) or mixtures of any of these.

In one aspect, the invention features methods that include reducing one or more dimensions of individual pieces of biomass; treating biomass, such as size-reduced biomass, using a treatment method that changes the molecular structure of the biomass; and, optionally, subjecting the biomass to a primary process to form a product. At least one of the size-reduction and treating steps comprises treating the biomass feedstock with a screw extrusion process. The treatment method may include, or further include, for example, irradiation, sonication, pyrolysis, and oxidation. The screw extrusion process can be used, for example, to reduce the dimensions of a feedstock, pulp the feedstock, or the screw extruder can be used as a reaction vessel in which the feedstock undergoes a chemical reaction, such as along its length as the feedstock is being conveyed. The screw extrusion step can include co-extruding the biomass with a separated portion of the biomass and/or with one or more other materials, which can be organic, inorganic, or mixtures of the two. The one or more other materials can be, for example, solid or liquid, and in some instances can include a gaseous material.

The primary process may be, for example, fermentation. The primary process is preferably performed after the screw extrusion process and after any necessary detoxification step, e.g., to remove any furan compounds produced. For example, after extrusion the material can be added to a fermentation vessel that has a volume of, for example, 50,000 L, 100,000 L, 500,000 L, or more.

In some implementations, the treatment method can include irradiation and sonication, used in combination. The radiation can be ionizing radiation, for example, in the form of an electron beam or gamma rays. In some embodiments, irradiating includes applying two or more radiation sources, such as gamma rays or x-rays (e.g., bremsstrahlung radiation) and a beam of electrons, e.g., an accelerated beam of electrons in which each electron has been accelerated to 1, 2, 3, 5 or even 10 MeV. In some embodiments, at least one of the treatment methods, e.g., irradiation, is performed on the biomass feedstock while the biomass feedstock is exposed to air or air enriched with oxygen or some other oxidizing gas, such as ozone. In specific embodiments, the electron beam radiation is applied at a total dosage of about 10 MRad and the sonication is applied at a total energy of more than 5 $MJ/m^3$. The radiation can have a wavelength of, for example, from about 100 nm to about 280 nm. The radiation can be applied, for example, at a total dose of between about 10 Mrad and about 150 Mrad, such as at a dose rate of about 0.5 to about 10 Mrad/day, or 1 Mrad/s to about 10 Mrad/s. Sonication can be performed at a frequency of between about 15 kHz and about 25 kHz, such as between about 18 kHz and 22 kHz.

Irradiation can precede sonication, sonication can precede irradiation, or irradiation and sonication can performed at or about the same time. In some cases, irradiation can be performed during the screw extrusion process.

The change in molecular structure of the biomass feedstock can include a change in any one or more of level of recalcitrance, an average molecular weight, average crystallinity, surface area, degree of polymerization, porosity, degree of branching, degree of grafting, domain size of the biomass and molecular make-up of the biomass. In some embodiments, the change in molecular structure of the biomass feedstock includes a decrease in either one or both of an average molecular weight and average crystallinity of the biomass or an increase in either one or both of surface area and porosity of the biomass.

In another aspect, the invention features methods of making products, such as combustible fuels, that include providing a material that includes a carbohydrate produced by a process that includes treating a biomass feedstock with radiation, sonication, pyrolysis, and/or oxidation; subjecting the feedstock to a screw extrusion process; and contacting the material with a microorganism having the ability to convert at least a portion, e.g., at least about 1 percent by weight, of the material to the product, such as a combustible fuel.

The microorganism can be, e.g., a bacterium or a yeast. Examples of fuels produced include one or more of hydrogen, alcohols, and hydrocarbons. For example, the alcohols can be ethanol, n-propanol, isoproanol, n-butanol, or mixtures of these. Converting can include fermenting the material to the product, such as the combustible fuel. During the screw extrusion process, the biomass can be contacted with a chemical, such as an oxidizing agent, an acid, or a base.

In some embodiments, the method does not include hydrolyzing the biomass with an acid or a base. For example, in some embodiments, at least about seventy percent by weight of the biomass is un-hydrolyzed, e.g., at least at 95 percent by weight of the biomass has not been hydrolyzed. In specific embodiments, substantially none of the biomass has been hydrolyzed.

In some embodiments, the screw extrusion process is performed on biomass in which less than about 25 percent by weight of the biomass is wetted with a liquid, such as water. Specifically, in some embodiments, substantially none of the biomass is wetted with a liquid. The biomass can have, e.g., less than about five percent by weight retained water, measured at 25° C. and at fifty percent relative humidity.

Pressure can be utilized in one or more of the steps of the method. For example, at least one of the treatment methods, e.g., radiation, can be performed on the biomass under a pressure of greater than about 2.5 atmospheres, such as greater than 5 or 10 atmospheres. In some implementations, the screw extrusion step can be performed under a pressure of greater than about 20 atmospheres, e.g., from about 25 to about 200 atmospheres, or from about 50 to about 150 atmospheres.

The process can further include oxidizing, pyrolizing, or steam exploding the biomass, before, during or after the treatment step.

In particular embodiments, the cellulosic and/or lignocellulosic material is size-reduced by freeze grinding. For example, the material can be comminuted in a freezer mill such that each material is cooled to a temperature below 25° C., such as at or below 0° C., such as at or below the normal atmospheric sublimation temperature of dry ice, or at or below the normal atmospheric boiling point of liquid nitrogen. Grinding biomass in a freezer mill is described in U.S. Provisional Patent Application Ser. No. 61/081,709, entitled "Cooling and Processing Materials," which is incorporated herein by reference in its entirety.

Examples of biomass feedstock include paper, paper products, paper waste, wood, particle board, sawdust, agricultural waste, sewage, silage, grasses, rice hulls, bagasse, cotton, jute, hemp, flax, bamboo, sisal, abaca, straw, corn cobs, corn stover, switchgrass, alfalfa, hay, rice hulls, coconut hair, cotton, synthetic celluloses, seaweed, algae, or mixtures of these. The biomass can be or can include a natural or a synthetic material.

In some embodiments, the biomass includes a first cellulose having a first number average molecular weight and the carbohydrate material comprises a second cellulose having a second number average molecular weight lower than the first number average molecular weight. For example, the second number average molecular weight is lower than the first number average molecular weight by more than about one-fold. In some embodiments, the first cellulose has a first crystallinity, and the second cellulose has a second crystallinity lower than the first crystallinity. For example, the second crystallinity can be lower than the first crystallinity by more than about 10 percent.

In some embodiments, the first cellulose can have a first level of oxidation and the second cellulose has a second level of oxidation higher than the first level of oxidation.

The biomass feedstock can be prepared by shearing a biomass fiber source to provide a fibrous material. For example, the shearing can be performed with a rotary knife cutter. The fibers of the fibrous material can have, e.g., an average length-to-diameter ratio of greater than 5/1. The fibrous material can have, e.g., a BET surface area of greater than 0.25 m²/g.

In some embodiments, the carbohydrate can include one or more β-1,4-linkages and having a number average molecular weight between about 3,000 and 50,000.

In some implementations, the treated biomass material can further include a buffer, such as sodium bicarbonate or ammonium chloride, an electrolyte, such as potassium chloride or sodium chloride a growth factor, such as biotin and/or a base pair such as uracil, a surfactant, a mineral, or a chelating agent.

Further examples of products that may be produced using the methods disclosed herein include mono- and polyfunctional C1-C6 alkyl alcohols, mono- and poly-functional carboxylic acids, C1-C6 hydrocarbons, and combinations thereof. Specific examples of suitable alcohols include methanol, ethanol, propanol, isopropanol, butanol, ethylene glycol, propylene glycol, 1,4-butane diol, glycerin, and combinations thereof. Specific example of suitable carboxylic acids include formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid, γ-hydroxybutyric acid, and combinations thereof. Examples of suitable hydrocarbons include methane, ethane, propane, pentane, n-hexane, and combinations thereof. Many of these products may be used as fuels.

The term "fibrous material," as used herein, is a material that includes numerous loose, discrete and separable fibers. For example, a fibrous material can be prepared from a bleached Kraft paper fiber source by shearing, e.g., with a rotary knife cutter.

The term "screen," as used herein, means a member capable of sieving material according to size. Examples of screens include a perforated plate, cylinder or the like, or a wire mesh or cloth fabric.

The term "pyrolysis," as used herein, means to break bonds in a material by the application of heat energy. Pyrolysis can occur while the subject material is under vacuum, or immersed in a gaseous material, such as an oxidizing gas, e.g., air or oxygen, or a reducing gas, such as hydrogen.

Oxygen content is measured by elemental analysis by pyrolyzing a sample in a furnace operating at 1300° C. or above.

The terms "biomass" refers to any non-fossilized, i.e., renewable, organic matter. The various types of biomass include plant biomass (defined below), animal biomass (any animal by-product, animal waste, etc.) and municipal waste biomass (residential and light commercial refuse with recyclables such as metal and glass removed).

The term "plant biomass" and "lingocellulosic biomass" refer to virtually any plant-derived organic matter (woody or non-woody) available for energy on a sustainable basis. Plant biomass can include, but is not limited to, agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally grass crops, such as switchgrass and the like have potential to be produced on a large-scale as another plant biomass source. For urban areas, the best potential plant biomass feedstock includes yard waste (e.g., grass clippings, leaves, tree clippings, and brush) and vegetable processing waste. "Lignocellulosic feedstock," is any type of plant biomass such as, but not limited to, non-woody plant biomass, cultivated crops, such as, but not limited to, grasses, for example, but not limited to, C4 grasses, such as switchgrass, cord grass, rye grass, miscanthus, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may include cellulosic waste material such as, but not limited to, newsprint, cardboard, sawdust, and the like.

Lignocellulosic feedstock may include one species of fiber or alternatively, lignocellulosic feedstock may include a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

For the purposes of this disclosure, carbohydrates are materials that are composed entirely of one or more saccharide units or that include one or more saccharide units. Carbohydrates can be polymeric (e.g., equal to or greater than 10-mer, 100-mer, 1,000-mer, 10,000-mer, or 100,000-mer), oligomeric (e.g., equal to or greater than a 4-mer, 5-mer, 6-mer, 7-mer, 8-mer, 9-mer or 10-mer), trimeric, dimeric, or monomeric. When the carbohydrates are formed of more than a single repeat unit, each repeat unit can be the same or different.

Examples of polymeric carbohydrates include cellulose, xylan, pectin, and starch, while cellobiose and lactose are examples of dimeric carbohydrates. Examples of monomeric carbohydrates include glucose and xylose.

Carbohydrates can be part of a supramolecular structure, e.g., covalently bonded into the structure. Examples of such materials include lignocellulosic materials, such as that found in wood.

A combustible fuel is a material capable of burning in the presence of oxygen. Examples of combustible fuels include ethanol, n-propanol, n-butanol, hydrogen and mixtures of any two or more of these.

Swelling agents as used herein are materials that cause a discernable swelling, e.g., a 2.5 percent increase in volume over an unswollen state of cellulosic and/or lignocellulosic materials, when applied to such materials as a solution, e.g., a water solution. Examples include alkaline substances, such as sodium hydroxide, potassium hydroxide, lithium hydroxide and ammonium hydroxides, acidifying agents, such as mineral acids (e.g., sulfuric acid, hydrochloric acid and phosphoric acid), salts, such as zinc chloride, calcium carbonate, sodium carbonate, benzyltrimethylammonium sulfate, and basic organic amines, such as ethylene diamine.

A "sheared material," as used herein, is a material that includes discrete fibers in which at least about 50% of the discrete fibers, have a length/diameter (L/D) ratio of at least about 5, and that has an uncompressed bulk density of less than about 0.6 g/cm$^3$. A sheared material is thus different from a material that has been cut, chopped or ground.

Changing a molecular structure of a biomass feedstock, as used herein, means to change the chemical bonding arrangement or conformation of the structure. For example, the change in the molecular structure can include changing the supramolecular structure of the material, oxidation of the material, changing an average molecular weight, changing an average crystallinity, changing a surface area, changing a degree of polymerization, changing a porosity, changing a degree of branching, grafting on other materials, changing a crystalline domain size, or an changing an overall domain size.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 19 and 20 are sectional views of an alternative discharge valve that can be used in the screw extruder of FIG. 13.

FIG. 21 is a schematic representation of an alternative dynamic seal that can be used in the screw extruder of FIG. 13.

FIG. 22 is a longitudinal section as seen from above of an alternative screw extruder.

FIG. 23 shows in its upper part a transverse partial cross-section on the line II-II in FIG. 22, and in its lower part a transverse partial cross-section on the line III-III in FIG. 22.

FIG. 24 is a longitudinal section seen from one side of another alternative screw extruder.

DETAILED DESCRIPTION

Figure 1:
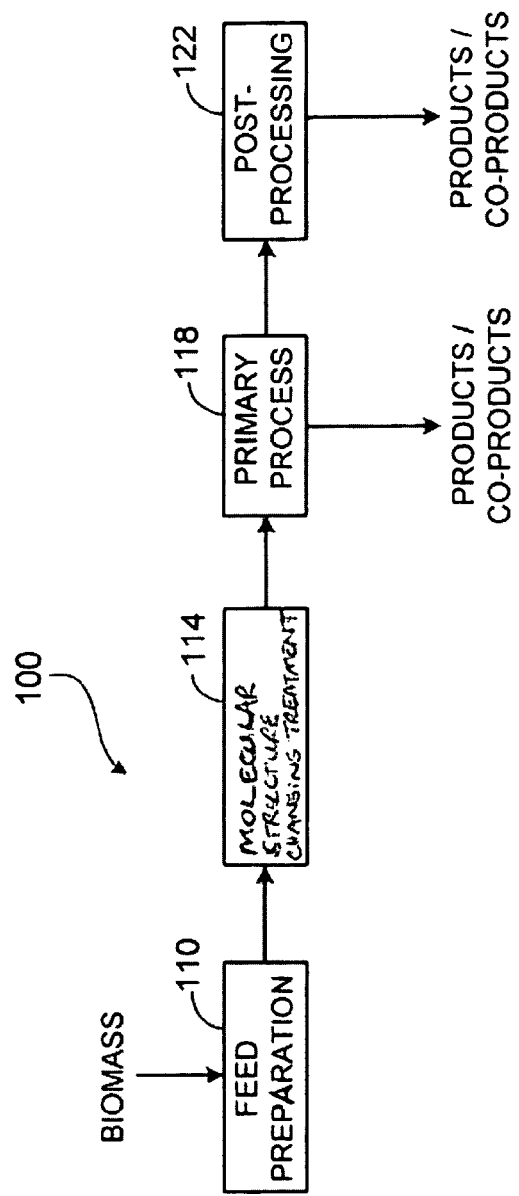
FIG. 1 is a block diagram illustrating conversion of biomass into products and co-products.

Biomass (e.g., plant biomass, animal biomass, and municipal waste biomass) can be processed to produce useful products such as fuels. Systems and processes are described herein that can utilize biomass feedstock materials, such as cellulosic and/or lignocellulosic materials, that are readily available, but that can be difficult to process. Feedstock materials are physically and/or chemically prepared for such processing by subjecting the feedstock materials to a screw extrusion step, which can result in a size reduction of raw feedstock materials and in some cases in densification, pulping, and/or hydrolysis (e.g., acid hydrolysis) of the feedstock material. If desired, prior to, during, or after the screw extrusion step, the feedstock can be treated or processed using one or more of radiation, sonication, oxidation, pyrolysis, and steam explosion. When utilized, the various treatment systems and methods can be used in combinations of two, three, or even four of these technologies.

In some cases, to provide materials that include a carbohydrate, such as cellulose, that can be converted by a microorganism to a number of desirable products, such as a combustible fuels (e.g., ethanol, butanol or hydrogen), feedstocks that include one or more saccharide units can be treated by any one or more of the processes described herein. Other products and co-products that can be produced include, for example, human food, animal feed, pharmaceuticals, and nutriceuticals. A number of examples are presented that range from bench scale implementations of individual treatment methods to large scale biomass processing plants.

Types of Biomass

Generally, any biomass material that is or includes carbohydrates composed entirely of one or more saccharide units or that include one or more saccharide units can be processed by any of the methods described herein. For example, the biomass material can be cellulosic or lignocellulosic materials.

For example, such materials can include paper, paper products, wood, wood-related materials, particle board, grasses, rice hulls, bagasse, cotton, jute, hemp, flax, bamboo, sisal, abaca, straw, corn cobs, rice hulls, coconut hair, algae, seaweed, cotton, synthetic celluloses, or mixtures of any of these.

Fiber sources include cellulosic fiber sources, including paper and paper products (e.g., polycoated paper and Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; and synthetic fiber sources, e.g., extruded yarn (oriented yarn or un-oriented yarn). Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105.

In some embodiments, the carbohydrate is or includes a material having one or more β-1,4-linkages and having a number average molecular weight between about 3,000 and 50,000. Such a carbohydrate is or includes cellulose (I), which is derived from (β-glucose 1) through condensation of β(1→4)-glycosidic bonds. This linkage contrasts itself with that for α(1→4)-glycosidic bonds present in starch and other carbohydrates.

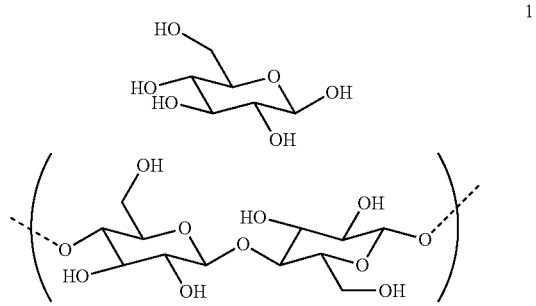

Blends of any of the above materials may also be used.

Exemplary Systems for Treating Biomass

FIG. 1 shows a system 100 for converting biomass, particularly biomass with significant cellulosic and lignocellulosic components, into useful products and co-products. System 100 includes a feed preparation subsystem 110, a pretreatment subsystem 114, a primary process subsystem 118, and a post-processing subsystem 122. Feed preparation subsystem 110 receives biomass in its raw form, physically prepares the biomass for use as feedstock by downstream processes (e.g., reduces the size of and homogenizes the biomass), and stores the biomass both in its raw and feedstock forms. Biomass feedstock with significant cellulosic and lignocellulosic components can have a high level of recalcitrance, often exemplified by a high average molecular weight and crystallinity that can make processing the feedstock into useful products (e.g., fermenting the feedstock to produce ethanol) difficult.

Treatment subsystem 114 receives feedstock from the feed preparation subsystem 110 and prepares the feedstock for use in primary production processes by, for example, reducing the average molecular weight and crystallinity of the feedstock. Primary process subsystem 118 receives treated feedstock from treatment subsystem 114 and produces useful products (e.g., ethanol, other alcohols, pharmaceuticals, and/or food products). In some cases, the output of primary process subsystem 118 is directly useful but, in other cases, requires further processing provided by post-processing subsystem 122. Post-processing subsystem 122 provides further processing to product streams from primary process system 118 which require it (e.g., distillation and denaturation of ethanol) as well as treatment for waste streams from the other subsystems. In some cases, the co-products of subsystems 114, 118, 122 can also be directly or indirectly useful as secondary products and/or in increasing the overall efficiency of system 100. For example, post-processing subsystem 122 can produce treated water to be recycled for use as process water in other subsystems and/or can produce burnable waste which can be used as fuel for boilers producing steam and/or electricity.

The screw extrusion step discussed herein may take place as part of the feed preparation subsystem, for example to reduce the size of and/or homogenize the biomass feedstock. Alternatively, or in addition, screw extrusion may be performed as part of the treatment and/or primary process subsystems. In some cases, screw extrusion may be used to densify a fibrous material, as will be discussed in detail below. In some implementations, the screw extruder may be used as a reaction vessel, in which the biomass is subjected to a reaction such as hydrolysis.

The optimum size for biomass conversion plants is affected by factors including economies of scale and the type and availability of biomass used as feedstock. Increasing plant size tends to increase economies of scale associated with plant processes. However, increasing plant size also tends to increase the costs (e.g., transportation costs) per unit of feedstock. Studies analyzing these factors suggest that the appropriate size for biomass conversion plants can range from 2000 to 10,000 dried tons of feedstock per day depending at least in part on the type of feedstock used. The type of feedstock can also impact plant storage requirements with plants designed primarily for processing feedstock whose availability varies seasonally (e.g., corn stower) requiring more on- or of-site feedstock storage than plants designed to process feedstock whose availability is relatively steady (e.g., waste paper).

Screw Extrusion

The processes disclosed herein advantageously employ at least one screw extrusion step in order to enhance the processing of biomass into useful products. As discussed above, the screw extrusion process can be performed at one or more points in the biomass processing system. Generally, the equipment and techniques used will be similar regardless of at what point in the process the screw extrusion step is performed. The general system and parameters for the screw extrusion step will now be discussed. To the extent that any of these parameters are varied depending upon when screw extrusion is performed, this will be mentioned in the following sections describing the subsystems of the biomass processing system 100.

The first system described, shown in FIGS. 13-20, may advantageously be used as reaction vessel, in which a reaction is performed, as will be discussed below. However, in some implementations this system can be used simply to grind, comminute or pulp the biomass feedstock, with or without application of heat or pressure. Moreover, while examples of chemical reactants are mentioned below, other chemical reactants or additives can be used, or in some implementations in which the screw extruder is not being used as a reaction vessel nothing may be added.

While single barrel screw extruders are discussed below and shown in the Figures, the term "screw extrusion," as used herein, includes co-extrusion. Thus, if desired, the screw extrusion step may include co-extrusion using a multi-barreled co-extruder. A multi-barreled co-extruder can have, for example, 2, 3, 4, 5, 6, 7, 8, 9, or 10 barrels. Such co-extruders are well known and thus are not illustrate herein. Co-extrusion may be utilized in a variety of ways. For example, the biomass may be separated into two or more fractions, which then are conveyed through separate barrels of the co-extruder. If desired, the fractions can be treated differently in the different barrels. For instance, one fraction can be oxidized by treatment with an oxidant, while another fraction can be subjected to steam and pressure but not oxidation. Alternatively or in addition, the multiple fractions may be different prior to their introduction to the co-extruder, for example one fraction may have a higher moisture content than another. In another embodiment, biomass is fed into one or more of the barrels while a non-biomass material is fed into one or more other barrels. The co-extruder may be used to deposit multiple layers one on top of another to form a multilayer extrudate. Alternatively, the multiple extrudates exiting the barrels can simply be mixed together. Generally, in this case, the co-extruder is utilized to allow the different fractions or materials to be treated differently during co-extrusion.

Moreover, if desired, two or more screw extruders (single barreled extruders and/or co-extruders in any desired combination), can be linked together in series. This can allow, for example, as series of screw extrusion steps to be performed under different conditions, or can allow a long residence time within a screw extruder barrel without the need for a single long screw extruder. In one example, biomass is first processed in a single barrel screw extruder, and then the resulting processed biomass is separated into two streams, which are fed into two barrels of a co-extruder.

The extrudate or co-extrudate can be a composite, e.g., in board or pellet form. Pellets generated by extrusion or co-extrusion can be used in other applications, for example in processes for manufacturing composite boards. Other uses for the extrudate or co-extrudate include pharmaceuticals, nutraceuticals, and food products.

Figure 13:
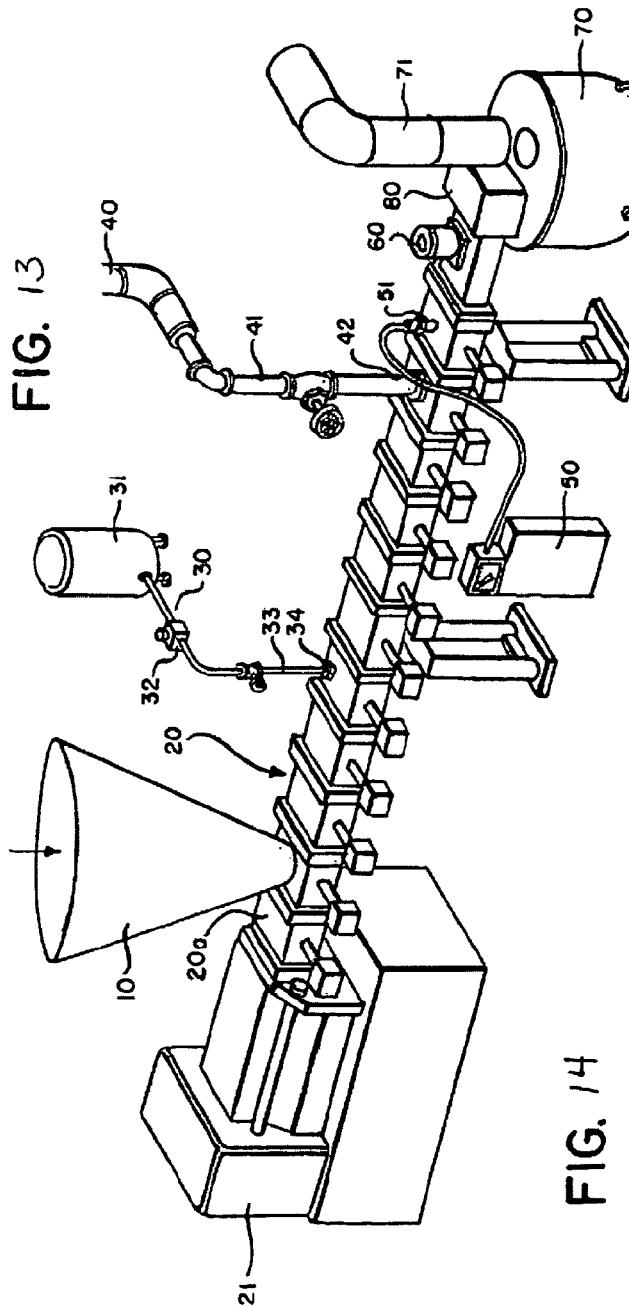
FIG. 13 is a perspective view of a screw extruder.
Figure 15:
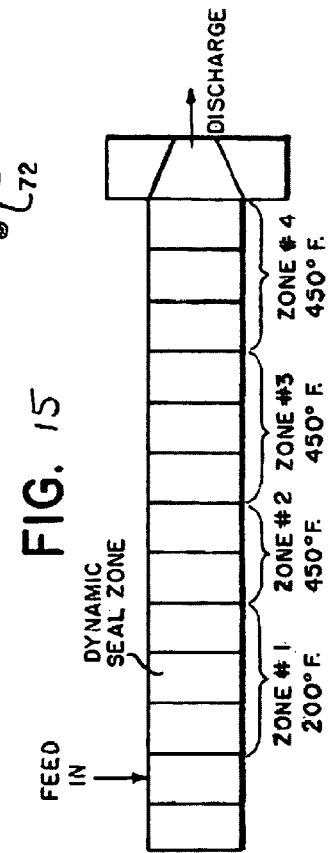
FIG. 15 is a schematic representation of the heat zones in the screw extruder of FIG. 13.
Figure 14:
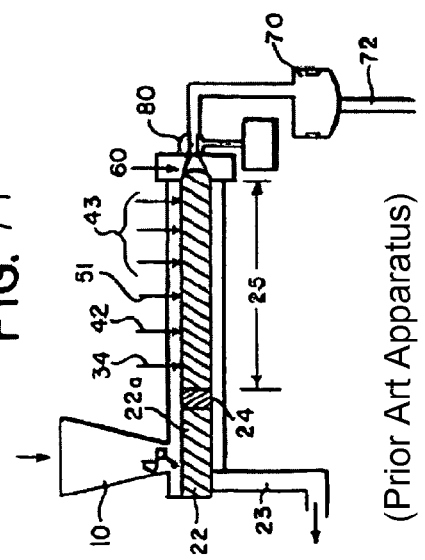
FIG. 14 is a sectional schematic view of the screw extruder of FIG. 13.
Figure 16:
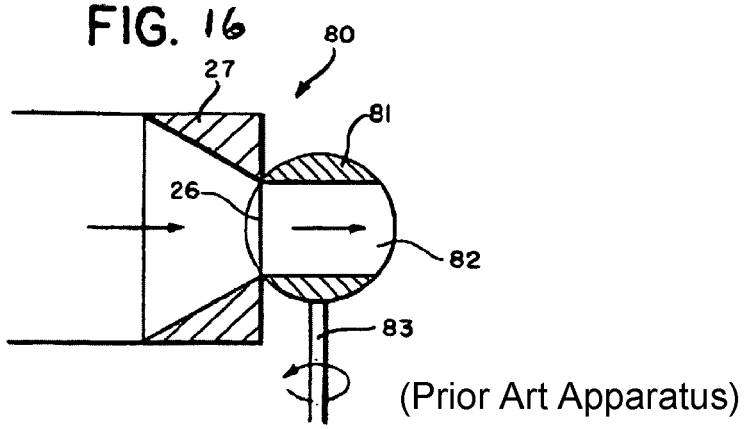
FIGS. 16 and 17 are sectional views of a discharge valve that can be used in the screw extruder of FIG. 13.

FIG. 13 shows a screw extruder 20, which may be, for example, a Werner & Pfleiderer ZDS-K 53 twin screw extruder. The screw extruder shown in FIG. 13 has two corotational screws therein driven by a motor 21, though counter-rotational arrangements can also be used. The housing 20a includes a feed inlet in which the material to be converted is received. Biomass feedstock, e.g., in the form of a slurry or in a dry or semi-dry state, is fed into the extruder 20 by means of a crammer feeder 10, which, as shown in FIG. 14, has screw elements for conveying the material into the extruder.

The extruder 20 includes a reaction zone 25 which is bounded on its inlet side by a dynamic seal zone 24 and bounded on its outlet side by a discharge valve 80. Upstream of the reaction zone is the inlet portion or preheating zone 22a of twin screws 22 wherein the fibrous input is first received and thereby conveyed into the reaction zone.

When the fibrous material is received in a slurry, much of the water of the slurry is removed in the process of the conveyance of the slurry into the reaction zone and for this purpose a dewatering drain 23 is provided upstream of the dynamic seal. Where the fibrous material is fed in dry form, the dewatering drain is not necessary since the liquid added thereto is just sufficient to act as a carrier or, in the case of hydrolysis, to act as the reactant, and therefore little or no water is removed during conveyance.

The apparatus further includes an input device 30 for adding an additive, for example an acid catalyst, an oxidant, a reducing agent, or a base. Input device 30 includes a tank 31 and a metering pump 32 which feeds the additive along a pipe 33 into an input port 34 in the extruder housing. The input port 34 is preferably at the beginning of the reaction zone 25, as shown, so that the additive acts on the reactants during substantially the entire residence time of the reactants in the reaction zone. However, the position of the input port 34 can be varied, for example depending upon the temperature in the reaction zone. (At higher temperatures, the reaction will generally take place faster and thus the additive can be introduced into the reaction zone at a position closer to the outlet thereof.)

In some implementations, it is advantageous for the reaction to take place at elevated temperatures and in order to bring this about in the most advantageous manner, steam can be added to add energy to the reaction zone to obtain a quick increase in temperature. For this, a steam supply device 40 is provided. The device 40 includes steam pipe 41 and steam input port 42. The steam may also be used as a supply of water for the hydrolysis of cellulose upon its condensation in the reaction zone.

It should also be noted that where the fibrous material is input into the extruder in a dry form, water may be added in the preheating zone before the dynamic seal 24 through input port 34.

Also provided along the extruder housing is a pressure indicator port 51 which, in conjunction with pressure indicator 50, enables a monitoring of the pressure within the reaction zone. Moreover, temperature input ports 43 are also provided to enable monitoring of the temperature within the various zones of the extruder assembly. These zones are set forth in FIG. 15 as zones 1-4 and show an example of a thermal configuration of the apparatus during use.

Further, at the outlet end of the reaction zone 25, a pressure release valve 60 is provided to provide pressure relief when the pressure within the reaction zone exceeds acceptable limits.

A quasi continuous or continuous discharge of the reactants from the extruder is effected by a discharge valve 80 which discharges the reactants into a collection vessel 70 which has a gas vent 71 and a flushing drain 72.

Figure 17:
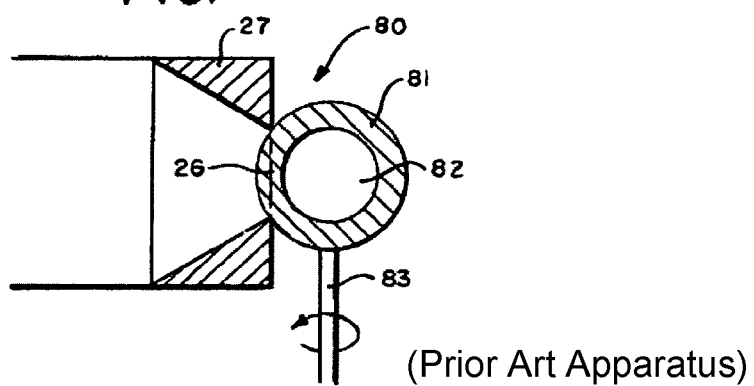
Figure 18:
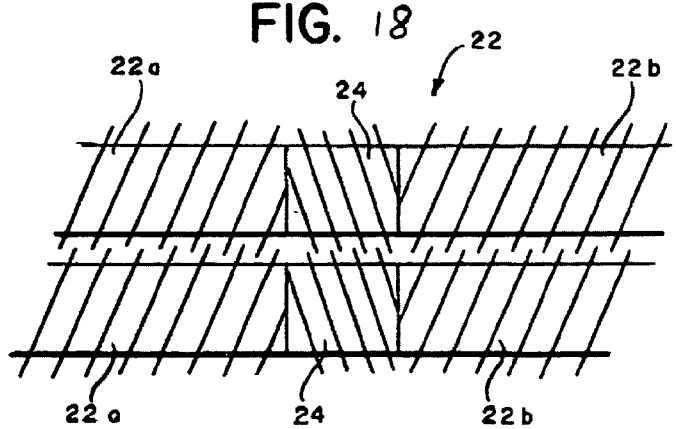
FIG. 18 is a schematic representation of a dynamic seal that can be used in the screw extruder of FIG. 13.

Turning to FIGS. 17-18, a discharge valve 80 that can be used in the screw extruder will be discussed in more detail. In this implementation, the discharge is brought about in a quasi-continuous manner by the use of a hydraulic actuated ball valve, for example a two inch Kamyr ball valve which has a 1.5" bore for heavy duty service. The ball 81 having the 1.5" bore 82 is rotatable on a shaft 83 which is hydraulically movable in a conventional manner. The ball 81 is situated at the outlet of the extruder which has a flange 27 for defining a valve aperture 26 which is coactive with the bore 82 to effect the quasi-continuous discharge of the reactants.

FIG. 17 shows the valve 80 fully opened, that is, the bore 82 is fully aligned with aperture 26. FIG. 18 shows the valve 80 in the fully closed position, that is, with bore 82 90 degrees out of phase with the aperture 26. The ball, in the case of the Kramyr ball valve, rotates 180 degrees every 20 seconds, thus taking 0.25 seconds to rotate. Accordingly, the valve is in the fully opened position about 10% of the time and thus for about 0.025 seconds each cycle.

Referring now to FIG. 19, the dynamic seal 24 is discussed in greater detail. The dynamic seal can be formed, for example, by providing left handed threads 24 in the area of the dynamic seal zone with right handed threads upstream thereof at screw area 22a and downstream thereof in screw area 22b. The left handed screw threads 24 act to form a dynamic plug which seals the reaction zone and prevents gases from escaping while continuously conveying the input into the reaction zone.

The dynamic seal, in conjunction with the valve 80, allows an elevated pressure and/or temperature to be maintained in the reaction zone, if desired, while enabling the screw elements to convey the feedstock into the reaction zone and out of the reaction zone.

The reaction zone inputs can be, for example, 25 pounds per hour dry biomass feedstock, 30 pounds per hour water, and 100 pounds per hour of a chemical reactant, e.g., an acid solution. For these inputs, the output can be, for example, a 20% solids mixture including 6 pounds per hour glucose, 9 pounds per hour cellulose, 5 pounds per hour lignin, 5 pounds per hour hemi cellulose or decomposed products, 100 pounds per hour water. The composition in the reaction zone will vary with the feed and the product composition also varies with the feed and the reaction conditions.

The feed material for wet feeds can have a consistency of, for example, 5% to 50% slurry, with a limited viscosity. Any of the biomass feedstocks discussed herein can be used. Preferably, the material has an average particle size between about 0.01 and about 250 µm, e.g., between about 0.1 and about 100 µm, or between about 0.250 and about 50 µm. The particle size deviation may be, for example, ±6 times the average particle size, 3 times the average particle size, or 1 times the average particle size. It is generally preferred that the particles have circular or plate-like shapes.

The feed rate can vary, depending upon the consistency of the feed material and the RPM of the screw elements, but is preferably very high, to facilitate use in a high throughput process. For example, for a 50,000,000 gal/year ethanol plant, throughput is about 57 tons/hour (114,000 lb/hour) for biomass that yields 100 gal/ton. Thus, it is preferred that the feed rate be at least 50,000 lb/hour, more preferably at least 100,000 lb/hour. To achieve these high feed rates, a very large swale is required. Accordingly, it is generally necessary that the screw extruder be very large, and/or that a plurality of screw extruders operate in parallel.

The reaction temperature can vary, for example from about 350° F. to about 550° F. at 1000 psi, and may also be higher depending upon the available steam pressure and the ability to discharge quickly. Alternate energy transfer modes are possible such as superheated steam or water or direct heat. The thermal configuration is such that all of the zones 2-4 are interchangable and can vary in length from 1 to 3 barrel sections. The preheating zone temperature can vary from about 32° F. to about 212° F. and the reaction zone temperatures can vary from about 350° F. to about 550° F.

The reaction pressure can vary, for example from about 135 psi to about 3000 psi or higher, depending upon the available steam pressure and the ability to discharge quickly. In some implementations, the reaction pressure can be from about 200 to about 500 psi. In some implementations, the pressure in the screw extruder can be relatively low, e.g., less than 75 psi.

The acid concentration for the process can be from 0.1 to 10% acid injection at rates of from 0 to 300 pounds per hour. Alternative acids or other additives may be used, for example peroxides, e.g., hydrogen or benxoyl peroxide; bases, such as sodium hydroxide or lime; HCl; $HNO_3$; organic acids; or $SO_2$ gas.

The dewatering that will occur will vary with the screw speed and the crammer speed, as well as the screw configuration. It may vary from, for example, 80 pounds per hour at 100 pounds per hour feed up to 720 pounds per hour at 900 pounds per hour feed. The solids in the dewater outlet also vary, for example from 0.05% to 5%.

The screw configuration can have a total length 2250 mm, and a preplug feed zone that is 630 mm long of 30 mm pitch elements conveying material 30 mm forward per revolution. The plug zone can be, e.g., 30 mm long with a 90 mm left hand pitch. The reaction zone can be, e.g., 1590 mm long, with 45 mm pitch stainless steel elements. The sections of the screw can be changed, or the entire screw can be changed, to suit the requirements of various applications.

The forward conveying preheating zone 22a can be any combination of right handed elements up to 2000 mm in length with 30, 45, 60 or 90 mm pitch elements. Also included therein can be mixing, pulverizing, or kneading elements, to provide a homogeneous material to the dynamic seal zone 25. The dynamic seal zone which forms the dynamic plug can be from 15 to 360 mm and comprises 30, 45, 60 or 90 mm lefthanded pitch elements. The reaction zone comprises the righthanded forward conveying element which is up to 2000 mm in length and includes 30, 45, 60 or 90 mm pitch right handed elements. The discharge valve can be, for example, a 2" Kamyr ball valve with 1½" bore 20 second cycle at 0.25 seconds per 180 degree cycle.

The screw machine speed, in revolutions per minute (RPM), can vary, for example from about 40 RPM to about 750 RPM, e.g., about 50 RPM to about 300 RPM. The screw converter and the crammer feeder can operate from about 8% to about 100% of maximum, e.g., about 8% to about 15%. The torque also varies, for example, from about 20% to about 100% of maximum, e.g., about 50% to about 70%, based on the screw RPM, the crammer rate, the consistency of feed, the screw configuration, the temperature profile, rate of acid injection, conversion rate and discharge rate.

The glucose conversion depends on all of the parameters noted above such as residence time, acid concentration, temperature, mixing which all depend on the machine parameters and can vary from 5% to 95% of the theoretical conversion maximum.

FIGS. 19 and 20 show an alternative valve 80', configured to allow a continuous discharge of the reactants in response to a predetermined pressure in the reaction zone 25. The valve 80' comprises a spherical valve body 81 which coacts with the flanged end of the extruder housing 27 having the valve aperture 26 therein. The spherical valve body 81 is preferably a 2" valve body.

The valve body 81 is seated in a valve plate 82 which has a spring 85 acting thereon to bias the valve body 81 into the closed position shown in FIG. 18. The biasing is carried out by the use of four screws 83 which are fixed at one end into the flange portion 27 and have threaded portions 83*a* at the other end thereof. Fitted onto the threaded portions 83*a* is a plate 84 which is prevented from moving to the right by nuts 86 which are threadably engaged with the threaded portions 83*a*. The valve assembly is sealed by the plate 87, which is screwed by screws 88 onto the housing 89 so that the only egress of the discharge material through aperture 26 is through the outlet 90.

In use, when the pressure within the reaction zone 25 exceeds the force exerted on the valve body 81 by the spring 85, the valve body 81 is moved to the right as shown in FIG. 20 and the discharge passes through the aperture 26 and through the outlet 90. When the screw extruder is in use, the pressure within the reaction zone will be continuously maintained so that, after the initialization of the process, the valve body 81 will remain in the open position and the discharge will continually pass through the valve 80'.

The pressure at which the valve 80' will be maintained in the continuously open position (FIG. 20) can be preset by use of the aforementioned nuts 86 which engage with the threaded portions 83*a*. In order to increase the selected pressure, the nuts 86 are turned clockwise to move the plate 84 to the left, thereby increasing the force that the spring 85 exerts on the plate 82 and thereby the valve body 81. Accordingly, the pressure can be decreased by reversing the above-mentioned process.

As shown in FIG. 21, the dynamic seal zone 24 can, in some implementations, be formed by the use of a radially recessed unthreaded screw section 240 on each screw, with optional left handed screw sections 24*a* upstream thereof and 24*b* downstream thereof. The unthreaded radially recessed portions 240 with the optionally left handed screw thread portions 24*a*, 24*b*, when taken in conjunction with the right hand screw threaded portions 22*a* upstream thereof and 22*b* downstream thereof, act to produce the dynamic plug which seals the reaction zone and prevents gases from escaping through the input, while enabling the fed-in material to be conveyed thereby into the reaction zone.

The dynamic seal, in conjunction with the valve means 80, maintains the elevated pressure and, where desirable, the elevated temperature in the reaction zone while enabling the screw elements to convey the fed-in material into the reaction zone and out of the reaction zone and to enable the reaction process to take place therein.

In some implementations, a screw extruder is used for grinding and reducing the recalcitrance of the biomass. For example a screw extruder can be used to delignify of the biomass feedstock. Example of suitable screw extruders for performing such a process are shown in FIGS. 22-24.

FIGS. 22 and 23 show a screw extruder that includes a pair of parallel shafts 601, 602, each provided with a helicoidal surface 603, 604, respectively, the shafts being arranged so that the surfaces 603, 604 interpenetrate. Each shaft is mounted at each end in a bearing 611, 612, 621, 622, the bearings being mounted in the ends of a casing 605 surrounding the shafts 601, 602.

The two shafts are rotated simultaneously by a motor 606 through two reduction gears 661, 662, each comprising a pinion mounted on an extension 610, 620 of the respective shaft beyond the corresponding bearing 611, 622. The two reduction gears are arranged head-to-tail, one at each end of the casing 605. The reduction gears are arranged so that the two shafts are rotated at the same speed and in the same direction by the motor 606. Two openings 651, 652 are provided in the casing 605, one at each end of the casing, the opening 651 being arranged at an upstream end of the helicoidal surfaces and the opening 652 being arranged at a downstream end of the helicoidal surfaces. The shafts are rotated in a direction to cause advancement of material fed into the machine through the opening 651 towards the opening 652.

The pitches of the helicoidal surfaces 603, 604 vary along the length of the shafts 601 and 602 so as to define successive zones with different pitches. In the simplest embodiment, as shown in FIG. 22, the helicoidal surfaces have a zone A of wide pitch in which material introduced through the inlet opening 651 advances downstream, and a "braking" zone B in which the pitch of the surfaces is reversed, the "braking" zone extending substantially over the final third of the shafts up to the outlet opening 652. The material introduced through the opening 651 is driven along the shafts towards the opening 652 and braked on entering the zone B, in which the helicoidal surfaces tend to push it in the opposite direction.

In this braking zone, the helicoidal surfaces are provided with apertures or windows 630 and 640 which may extend from the axis up to the outer edge of the surfaces. The size and separation of these windows can be chosen at will, and the windows allow, in particular, progressive and possibly selective movement of the material downstream as the grinding progresses.

The pulp leaves via the opening 652 practically at atmospheric pressure. There is thus no need for the machine to be fitted with a convergent nozzle, which means that the bearings 611, 612, 621, 622 can be mounted at each end of each shaft 601, 602 and the reduction gears can be fitted at both ends of the casing, as shown in FIG. 22.

Enclosures 607 may be arranged along the casing to allow the temperature of the zones to be precisely controlled by means of controlled heating and cooling. Preferably, induction heating is used, as this enables the temperature to be controlled particularly accurately. Steam may be introduced to the casing if desired.

Material introduced through opening 651 is driven downstream by the rotation of the shafts. Also, since the shafts turn in the same direction, a pumping action is obtained which enables the material to be driven downstream even when the spaces between the helicoidal surface are not filled up. In zone A the material spreads out in the form of a thin layer along the helicoidal surfaces, which progressively fill up. The material tends to be oriented in a homogeneous manner and is subjected, especially in the portion 634 (FIG. 23) where the helicoidal surfaces inter-penetrate, to combined compression and shear forces, the former due mainly to the inter-penetration of the surfaces and the latter due mainly to the rotation of the shafts in the same direction, which prepares the way for grinding. Further, the rotation of the helicoidal surfaces in the same direction produces a churning of the material which favors its homogenization. The temperature rises due to friction, but can be controlled and held at a required level by cooling the casing, without diluting the driven material.

At the end of zone A, the threads progressively fill up due to the braking of the circulation of the material caused by reversing the pitch of the surfaces in zone B. At the entry to zone B the reversal of the threads produces a considerable accumulation of material, which creates a zone of high compression. It is in zone B that grinding is finished, the braking effect due to reversing the surfaces reinforcing the combined action of the compression and shear forces.

The material is therefore held in this zone for a longer period, and undergoes a mixing which favors its homogenization. The windows 630 and 640 formed in the helicoidal surfaces permit the material to advance downstream as it is ground, the less well ground parts being held longer in the working area.

A highly concentrated mechanical pulp with good mechanical properties is extracted from the opening 652.

In the manufacture of screw extruders for plastics materials, a modular form of construction is often used, each screw consisting of sections attached together and threaded on to a central shaft. This form of construction can be used to produce helicoidal surfaces having successive zones with different pitches adapted to the required end result. The driving speed can be varied along the shaft, and likewise the pressure in the material. The surfaces may include, for example, several portions with reversed pitch provided with windows for the passage of the material and acting as braking zones separated from one another in which continuous plugs would be formed. By varying the pitch and the number and size of the windows, the plugs can be made more or less dense. It is then possible, with the aid of a pressure pump or any other known means, to inject a fluid either into a braking zone or between two plugs. The fluid could, for example, be superheated water, or steam or a chemical reagent which is preferably heated. Injecting this hot fluid under pressure can greatly facilitate its penetration into the material, e.g., wood fibers, and accelerate the grinding process.

Depending on the injection pressure, the viscosity of the reagent fluid injected, and the pitch of the helicoidal surfaces, several injection points may be provided, for various fluids moving either in the same direction as the material or against the flow of the material.

FIG. 24 shows another embodiment of a screw extruder. The extruder includes a zone I, in which the helicoidal surfaces have a fairly wide pitch and the raw material is impregnated with steam. In this zone the casing is fitted with an induction heating element 671. The material is introduced through an opening 651 and the steam taken off through an opening 653, which may be connected to a vacuum pump, at the end of the zone.

In zone II a first cooking stage can be carried out in the presence of chemical reagents introduced through an opening 654. A high pressure can be produced in this zone, and the required temperature obtained by means of a heating element 672. As mentioned above, the effect of pumping the material between the helicoidal surfaces enables the chips to be moved along in a thin film, which greatly facilitates access of the reagents to the chips and precise regulation of the reaction temperature, the more so because the rotation of the surfaces in the same direction can provide a churning of the layers in the zone 634 in which the surfaces inter-penetrate. A much more homogenous and better controlled treatment can thus be achieved.

In zone III the pitch is reversed and the threads are provided with windows 630 for controlled passage of the material downstream. The mechanical grinding of the raw material from zone II is essentially realized in this zone III. The grinding is carried out in accordance with the process described above. On entering the zone III, the material is heavily compressed under the effect of the braking due to the reversal of the pitch of the helicoidal surfaces. The windows formed in the surfaces enable the material to circulate downstream as the grinding progresses. Furthermore, the braking of the raw material at the entry to zone III produces a return of any excess liquid to zone II, where it can be taken off through the opening 655 for possible recycling.

The passage of the moist material between several interpenetrating screws inside a casing results in an upstream movement of the liquid and gaseous phases and a downstream movement of the solid phase.

In zone IV a second cooking stage is carried out under pressure. In this zone the pitch of the helicoidal surfaces may be widened to produce a thin film of pulp. The required temperature is obtained by means of a heating element 673. Oxygen may be introduced under pressure, if desired.

Zone V has close-pitched helicoidal surfaces with reverse threads and windows in which the pulp is again compressed, liquid moving upstream being taken off through an opening 656. An opening 657 for degassing may likewise be provided upstream. Thus, in zone V a final grinding operation is effected on any uncooked material.

A new chemical treatment zone 680 may also be provided downstream of zone V for introducing a chemical additive, which can be finally taken off through outlet orifice 652.

As the pulp leaves at atmospheric pressure, axial thrusts are considerably reduced. This greatly facilitates positioning the reduction gears at the two ends of the machine. In this way there is no limitation on the choice of pinion diameter, which permits the drive units to be less heavily loaded.

The helicoidal surfaces can be easily and quickly changed, so that the same plant can be readily adapted for carrying out various treatments merely by having available helicoidal surfaces with different profiles.

Parameters that influence the outcome of the screw extrusion process include the following: flight gap, tehtrahedron gap, calendar gap, side gap, residence time, and hot zone temperature (based on the decomposition temperature of the biomass.)

Screw extruders are disclosed, for example, in U.S. Pat. Nos. 4,088,528, 3,382,536, 4,316,747, 4,316,748, and 3,917,507, the full disclosures of which are incorporated herein by reference.

Feed Preparation

In some cases, methods of processing begin with a physical preparation of the feedstock, e.g., size reduction of raw feedstock materials. The physical preparation may be performed using the screw extrusion process discussed above. Alternatively, or prior to or even after screw extrusion, if size reduction is necessary physical preparation may be performed using other techniques, such as by cutting, grinding, shearing or chopping. In some cases, loose feedstock (e.g., recycled paper or switchgrass) is prepared by shearing or shredding. Screens and/or magnets can be used to remove oversized or undesirable objects such as, for example, rocks or nails from the feed stream.

Feed preparation systems can be configured to produce feed streams with specific characteristics such as, for example, specific maximum sizes, specific length-to-width, or specific surface areas ratios. As a part of feed preparation, the bulk density of feedstocks can be controlled (e.g., increased).

Size Reduction

In some embodiments, the material to be processed is in the form of a fibrous material that includes fibers provided by shearing a fiber source. For example, the shearing can be performed with a rotary knife cutter. A number of shearing steps are discussed below. Any or all of these shearing steps can be replaced by a screw extrusion step using the equipment discussed above or other suitable screw extrusion equipment.

Figure 2:
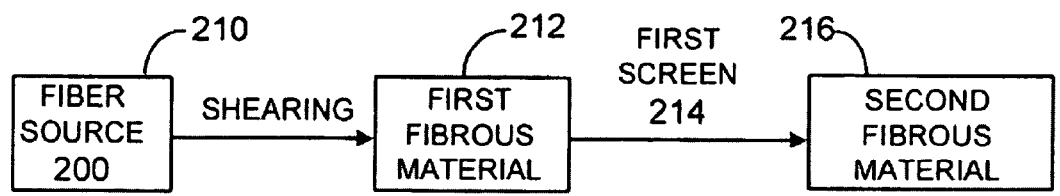
FIG. 2 is block diagram illustrating conversion of a fiber source into a first and second fibrous material.

For example, and by reference to FIG. 2, a fiber source 210 is sheared, e.g., in a rotary knife cutter, to provide a first fibrous material 212. The first fibrous material 212 is passed through a first screen 214 having an average opening size of 1.59 mm or less (1/16 inch, 0.0625 inch) to provide a second fibrous material 216. If desired, fiber source can be cut prior to the shearing, e.g., with a shredder. For example, when a paper is used as the fiber source, the paper can be first cut into strips that are, e.g., 1/4- to 1/2-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of fiber source and the passing of the resulting first fibrous material through first screen are performed concurrently. The shearing and the passing can also be performed in a batch-type process.

Figure 3:
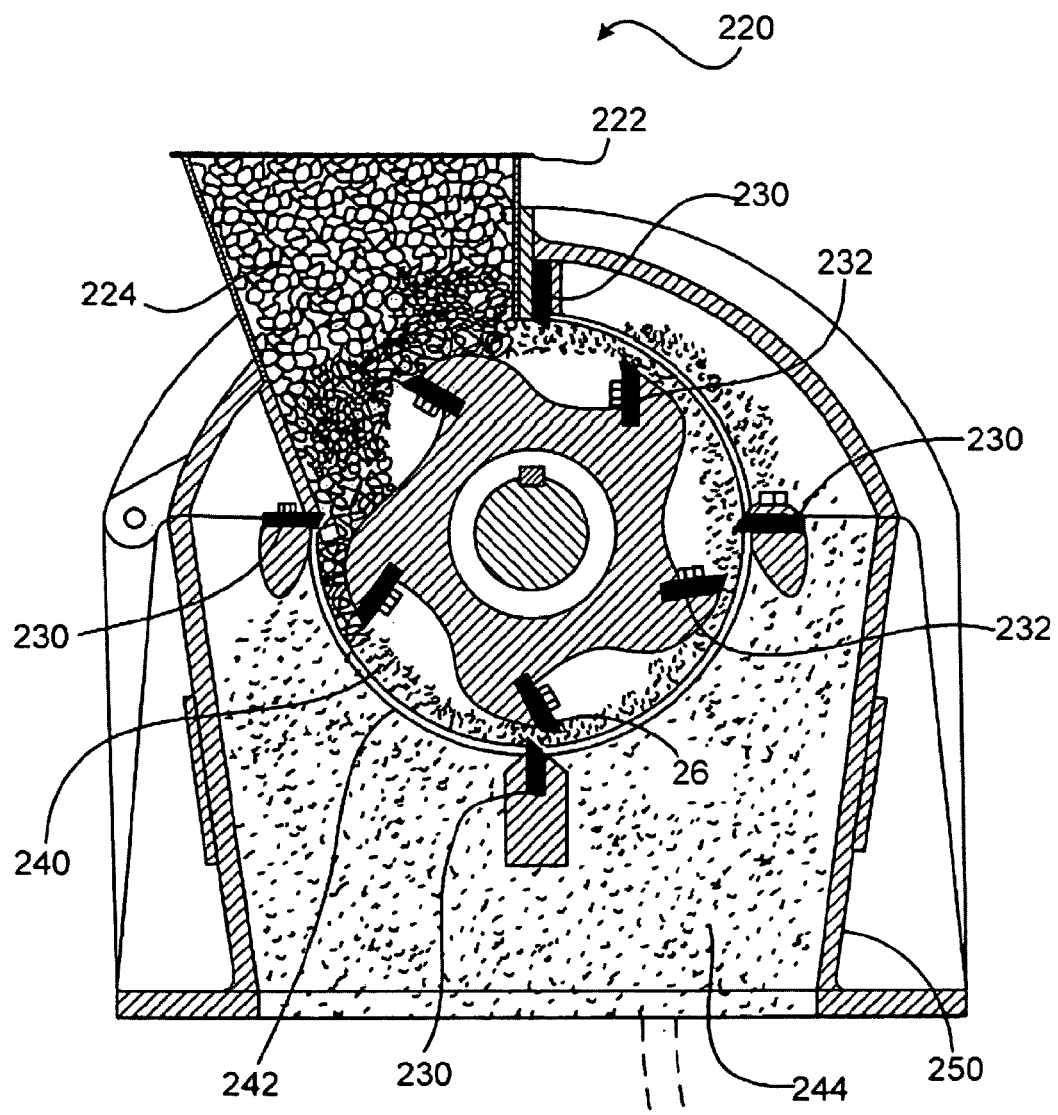
FIG. 3 is a cross-sectional view of a rotary knife cutter.

For example, a rotary knife cutter can be used to concurrently shear the fiber source and screen the first fibrous material. Referring to FIG. 3, a rotary knife cutter 220 includes a hopper 222 that can be loaded with a shredded fiber source 224 prepared by shredding fiber source. Shredded fiber source is sheared between stationary blades 230 and rotating blades 232 to provide a first fibrous material 240. First fibrous material 240 passes through screen 242, and the resulting second fibrous material 244 is captured in bin 250. To aid in the collection of the second fibrous material, the bin can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 252 is utilized to maintain the bin below nominal atmospheric pressure.

Shearing can be advantageous for "opening up" and "stressing" the fibrous materials, making the cellulose of the materials more susceptible to chain scission and/or reduction of crystallinity. The open materials can also be more susceptible to oxidation when irradiated.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, isopropanol.

The fiber source can also be sheared in under a gas (such as a stream or atmosphere of gas other than air), e.g., oxygen or nitrogen, or steam.

Other methods of making the fibrous materials include, e.g., stone grinding, mechanical ripping or tearing, pin grinding or air attrition milling.

If desired, the fibrous materials can be separated, e.g., continuously or in batches, into fractions according to their length, width, density, material type, or some combination of these attributes. For example, for forming composites, it is often desirable to have a relatively narrow distribution of fiber lengths.

For example, ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can also be separated, e.g., by using a high velocity gas, e.g., air. In such an approach, the fibrous materials are separated by drawing off different fractions, which can be characterized photonically, if desired. Such a separation apparatus is discussed in Lindsey et al, U.S. Pat. No. 6,883,667.

The fibrous materials can be irradiated immediately following their preparation, or they can may be dried, e.g., at approximately 105° C. for 4-18 hours, so that the moisture content is, e.g., less than about 0.5% before use.

If desired, lignin can be removed from any of the fibrous materials that include lignin. Also, to aid in the breakdown of the materials that include the cellulose, the material can be treated prior to irradiation with heat, a chemical (e.g., mineral acid, base or a strong oxidizer such as sodium hypochlorite) and/or an enzyme.

In some embodiments, the average opening size of the first screen is less than 0.79 mm (1/32 inch, 0.03125 inch), e.g., less than 0.51 mm (1/50 inch, 0.02000 inch), less than 0.40 mm (1/64 inch, 0.015625 inch), less than 0.23 mm (0.009 inch), less than 0.20 mm (1/128 inch, 0.0078125 inch), less than 0.18 mm (0.007 inch), less than 0.13 mm (0.005 inch), or even less than less than 0.10 mm (1/256 inch, 0.00390625 inch). The screen is prepared by interweaving monofilaments having an appropriate diameter to give the desired opening size. For example, the monofilaments can be made of a metal, e.g., stainless steel. As the opening sizes get smaller, structural demands on the monofilaments may become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g. a metal plate, having apertures, e.g., cut into the plate using a laser. In some embodiments, the open area of the mesh is less than 52%, e.g., less than 41%, less than 36%, less than 31%, less than 30%.

In some embodiments, the second fibrous is sheared and passed through the first screen, or a different sized screen. In some embodiments, the second fibrous material is passed through a second screen having an average opening size equal to or less than that of first screen.

Figure 4:
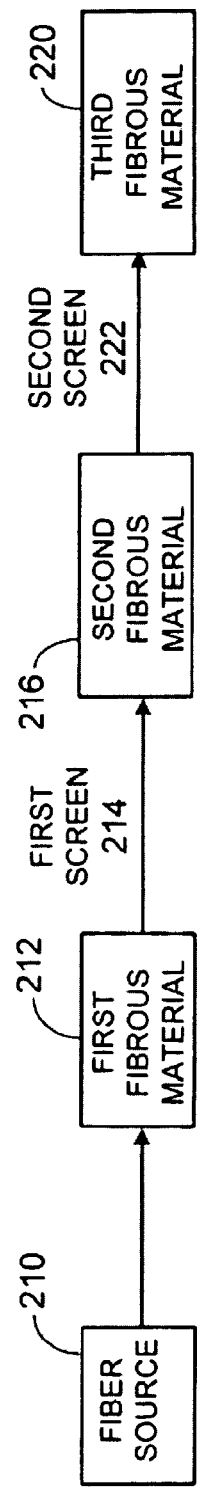
FIG. 4 is block diagram illustrating conversion of a fiber source into a first, second and third fibrous material.

Referring to FIG. 4, a third fibrous material 220 can be prepared from the second fibrous material 216 by shearing the second fibrous material 216 and passing the resulting material through a second screen 222 having an average opening size less than the first screen 214.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g. greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 µm and 50 µm, e.g., between about 10 µm and 30 µm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material to the average length-to-diameter ratio of the second fibrous material is, e.g., less than 1.5, e.g., less than 1.4, less than 1.25, less than 1.1, less than 1.075, less than 1.05, less than 1.025, or even substantially equal to 1.

In particular embodiments, the second fibrous material is sheared again and the resulting fibrous material passed through a second screen having an average opening size less than the first screen to provide a third fibrous material. In such instances, a ratio of the average length-to-diameter ratio of the second fibrous material to the average length-to-diameter ratio of the third fibrous material can be, e.g., less than 1.5, e.g., less than 1.4, less than 1.25, or even less than 1.1.

In some embodiments, the third fibrous material is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

Densification

Densified materials can be processed by any of the methods described herein.

A material, e.g., a fibrous material, having a low bulk density, e.g., a bulk density of 0.05 $g/cm^3$ or less, can be densified to a product having a higher bulk density.

For example, the screw extrusion processes discussed above can be used to densify a fibrous material, e.g., using braking zones as discussed in the Screw Extrusion section above.

Alternatively, a material composition can be densified using other techniques, for example by sealing the fibrous material in a relatively gas impermeable structure, e.g., a bag made of polyethylene or a bag made of alternating layers of polyethylene and a nylon, and then evacuating the entrapped gas, e.g., air, from the structure.

After densification, the fibrous material can have, e.g., a bulk density of greater than 0.3 $g/cm^3$, e.g., 0.5 $g/cm^3$, 0.6 $g/cm^3$, 0.7 $g/cm^3$ or more, e.g., 0.85 $g/cm^3$. After densification, the product can processed by any of the methods described herein, e.g., irradiated, e.g., with gamma radiation. This can be advantageous when it is desirable to transport the material to another location, e.g., a remote manufacturing plant, where the fibrous material composition can be added to a solution, e.g., to produce ethanol.

In the case of densification using an evacuated bag, after piercing the substantially gas impermeable structure the densified fibrous material can revert to nearly its initial bulk density, e.g., greater than 60 percent of its initial bulk density, e.g., 70 percent, 80 percent, 85 percent or more, e.g., 95 percent of its initial bulk density. To reduce static electricity in the fibrous material, an anti-static agent can be added to the material.

In some embodiments, the substantially gas-impermeable structure, e.g., bag, is formed of a material that dissolves in a liquid, such as water. For example, the structure can be formed from a polyvinyl alcohol so that it dissolves when in contact with a water-based system. Such embodiments allow densified structures to be added directly to solutions that include a microorganism, without first releasing the contents of the structure, e.g., by cutting.

Figure 5:
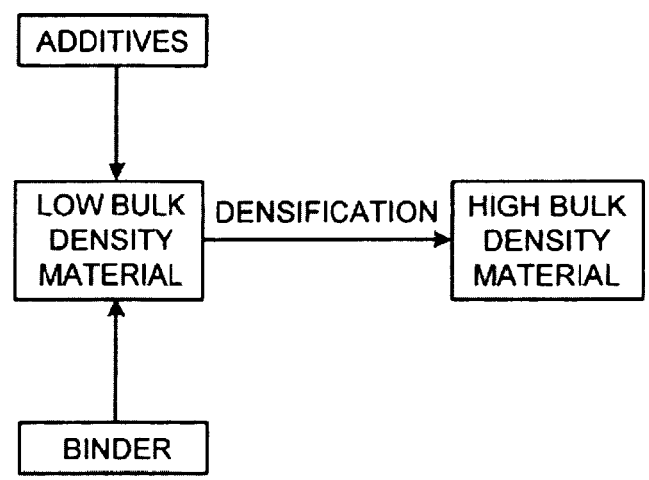
FIG. 5 is block diagram illustrating densification of a material.

Referring to FIG. 5, in other implementations a biomass material can be combined with any desired additives and a binder, and subsequently densified by application of pressure, e.g., by passing the material through a nip defined between counter-rotating pressure rolls or by passing the material through a pellet mill. During the application of pressure, heat can optionally be applied to aid in the densification of the fibrous material. The densified material can then be irradiated.

In some embodiments, the material prior to densification has a bulk density of less than 0.25 $g/cm^3$, e.g., 0.20 $g/cm^3$, 0.15 $g/cm^3$, 0.10 $g/cm^3$, 0.05 $g/cm^3$ or less, e.g., 0.025 $g/cm^3$. Bulk density is determined using ASTM D1895B. Briefly, the ASTM method of measuring bulk density involves filling a measuring cylinder of known volume with a sample and obtaining a weight of the sample. The bulk density is calculated by dividing the weight of the sample in grams by the known volume of the cylinder in cubic centimeters.

Figure 6:
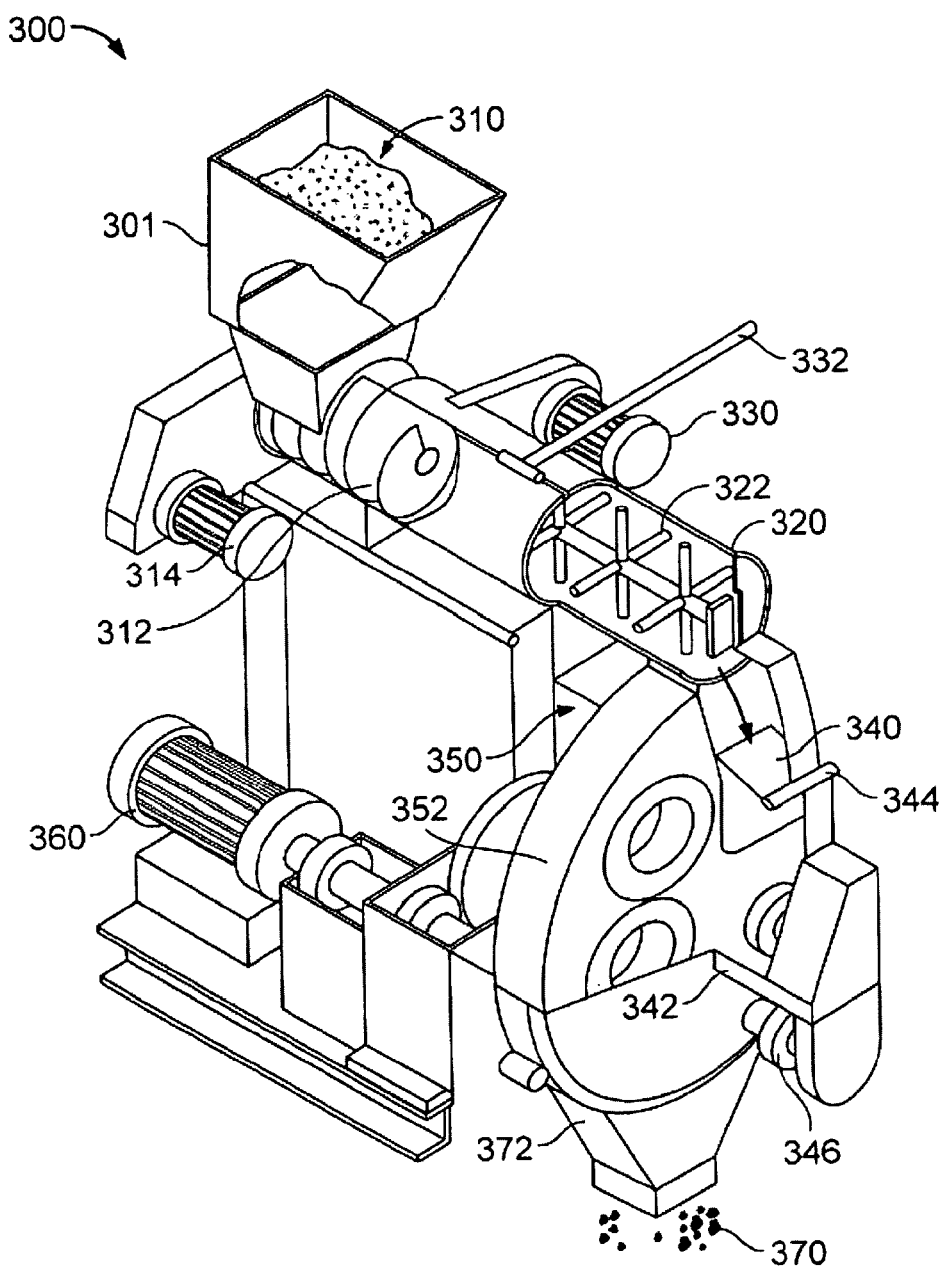
FIG. 6 is a perspective view of a pellet mill.

The densified fibrous material can be made in a pellet mill. In some cases, pelletizing is performed prior to screw extrusion, for example to make it easier to feed material into the screw extruder and thereby increase throughput. Referring to FIG. 6, a pellet mill 300 has a hopper 301 for holding undensified material 310 that includes a carbohydrate-containing materials, such as cellulose. The hopper communicates with an auger 312 that is driven by variable speed motor 314 so that undensified material can be transported to a conditioner 320 that stirs the undensified material with paddles 322 that are rotated by conditioner motor 330. Other ingredients, e.g., any of the additives and/or fillers described herein, can be added at inlet 332. If desired, heat may be added while the fibrous material is in conditioner. After conditioned, the material passes from the conditioner through a dump chute 340, and to another auger 342. The dump chute, as controlled by actuator 344, allows for unobstructed passage of the material from conditioner to auger. Auger is rotated by motor 346, and controls the feeding of the fibrous material into die and roller assembly 350. Specifically, the material is introduced into a hollow, cylindrical die 352, which rotates about a horizontal axis and which has radially extending die holes 250. Die 352 is rotated about the axis by motor 360, which includes a horsepower gauge, indicating total power consumed by the motor. Densified material 370, e.g., in the form of pellets, drops from chute 372 and are captured and processed, such as by irradiation.

The material, after densification, can be conveniently in the form of pellets or chips having a variety of shapes. The pellets can then be irradiated. In some embodiments, the pellets or chips are cylindrical in shape, e.g., having a maximum transverse dimension of, e.g., 1 mm or more, e.g., 2 mm, 3 mm, 5 mm, 8 mm, 10 mm, 15 mm or more, e.g., 25 mm. Another convenient shape for making composites includes pellets or chips that are plate-like in form, e.g., having a thickness of 1 mm or more, e.g., 2 mm, 3 mm, 5 mm, 8 mm, 10 mm or more, e.g., 25 mm; a width of, e.g., 5 mm or more, e.g., 10 mm, 15 mm, 25 mm, 30 mm or more, e.g., 50 mm; and a length of 5 mm or more, e.g., 10 mm, 15 mm, 25 mm, 30 mm or more, e.g., 50 mm.

Figure 7A:
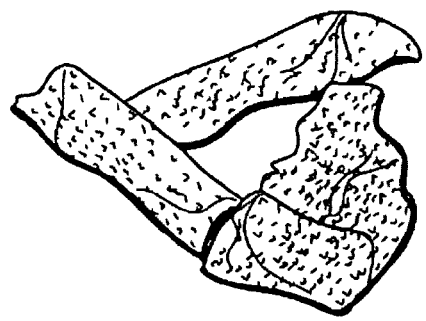
FIG. 7A is a densified fibrous material in pellet form.
Figure 7B:
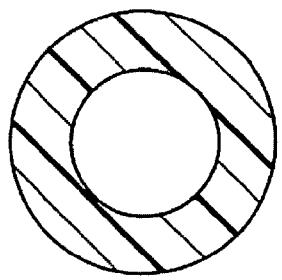
FIG. 7B is a transverse cross-section of a hollow pellet in which a center of the hollow is in-line with a center of the pellet.
Figure 7C:
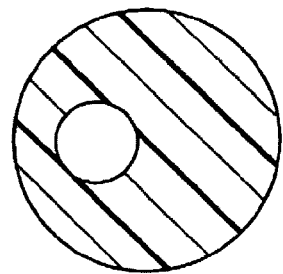
FIG. 7C is a transverse cross-section of a hollow pellet in which a center of the hollow is out of line with the center of the pellet.

Referring now FIG. 7A-7D, pellets can be made so that they have a hollow inside. As shown, the hollow can be generally in-line with the center of the pellet (FIG. 7B), or out of line with the center of the pellet (FIG. 7C). Making the pellet hollow inside can increase the rate of dissolution in a liquid after irradiation.

Figure 7D:
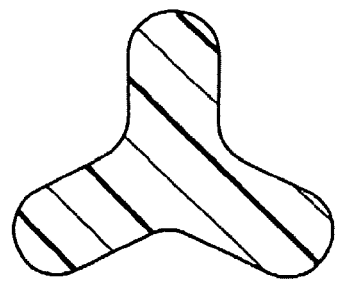
FIG. 7D is a transverse cross-section of a tri-lobal pellet.

Referring now to FIG. 7D, the pellet can have, e.g., a transverse shape that is multi-lobal, e.g., tri-lobal as shown, or tetra-lobal, penta-lobal, hexa-lobal or deca-lobal. Making the pellets in such transverse shapes can also increase the rate of dissolution in a solution after irradiation.

Molecular Structure Changing Treatments

Physically prepared feedstock can be treated for use in primary production processes by, for example, reducing level of recalcitrance, reducing the average molecular weight and crystallinity of the feedstock and/or increasing the surface area and/or porosity of the feedstock. Treatment processes can include one or more of irradiation, sonication, oxidation, pyrolysis, steam explosion, and screw extrusion, such as screw extrusion with acid injection along the extrusion barrel. The various pretreatment systems and methods can be used in combinations of two, three, or even four of these technologies. One or more of these techniques can be performed while the feedstock is being passed through the screw extruder, if desired. For example, the feedstock can be irradiated in one zone of the extruder, and steam can be injected under pressure into another zone of the extruder. In the case of sonication, an energy transmission medium, such as water, would be provided within the screw extruder.

Treatment Combinations

In some embodiments, biomass can be processed by applying two or more of any of the processes described herein, such as two or more of radiation, sonication, oxidation, pyrolysis, and steam explosion either with or without prior, intermediate, or subsequent feedstock preparation as described herein. The processes can be applied in any order (or concurrently) to the biomass, e.g., a cellulosic and/or lignocellulosic material. In other embodiments, materials that include a carbohydrate are prepared by applying three, four or more of any of the processes described herein (in any order or concurrently). For example, a carbohydrate can be prepared by applying radiation, sonication, oxidation, pyrolysis, and, optionally, steam explosion to a cellulosic and/or lignocellulosic material (in any order or concurrently). The provided carbohydrate-containing material can then be converted by one or more microorganisms, such as bacteria, yeast, or mixtures of yeast and bacteria, to a number of desirable products, as described herein. Multiple processes can provide materials that can be more readily utilized by a variety of microorganisms because of their lower molecular weight, lower crystallinity, and/or enhanced solubility. Multiple processes can provide synergies and can reduce overall energy input required in comparison to any single process.

For example, in some embodiments, feedstocks are provided that include a carbohydrate that is produced by a process that includes irradiating and sonicating (in either order or concurrently) a cellulosic and/or a lignocellulosic material, a process that includes irradiating and oxidizing (in either order or concurrently) a cellulosic and/or a lignocellulosic material, a process that includes irradiating and pyrolyzing (in either order or concurrently) a cellulosic and/or a lignocellulosic material, a process that includes irradiating and pyrolyzing (in either order or concurrently) a cellulosic and/or a lignocellulosic material, or a process that includes irradiating and steam-exploding (in either order or concurrently) a cellulosic and/or a lignocellulosic material. The provided feedstock can then be contacted with a microorganism having the ability to convert at least a portion, e.g., at least about 1 percent by weight, of the feedstock to the product, such as the combustible fuel, as described herein.

In some embodiments, the process does not include hydrolyzing the cellulosic and/or lignocellulosic material, such as with an acid or a base, e.g., a mineral acid, such as hydrochloric or sulfuric acid.

If desired, some or none of the feedstock can include a hydrolyzed material. For example, in some embodiments, at least about seventy percent by weight of the feedstock is an unhydrolyzed material, e.g., at least at 95 percent by weight of the feedstock is an unhydrolyzed material. In some embodiments, substantially all of the feedstock is an unhydrolyzed material.

Any feedstock or any reactor or fermentor charged with a feedstock can include a buffer, such as sodium bicarbonate, ammonium chloride or Tris; an electrolyte, such as potassium chloride, sodium chloride, or calcium chloride; a growth factor, such as biotin and/or a base pair such as uracil or an equivalent thereof; a surfactant, such as Tween® or polyethylene glycol; a mineral, such as such as calcium, chromium, copper, iodine, iron, selenium, or zinc; or a chelating agent, such as ethylene diamine, ethylene diamine tetraacetic acid (EDTA) (or its salt form, e.g., sodium or potassium EDTA), or dimercaprol.

When radiation is utilized, it can be applied to any sample that is dry or wet, or even dispersed in a liquid, such as water. For example, irradiation can be performed on cellulosic and/or lignocellulosic material in which less than about 25 percent by weight of the cellulosic and/or lignocellulosic material has surfaces wetted with a liquid, such as water. In some embodiments, irradiating is performed on cellulosic and/or lignocellulosic material in which substantially none of the cellulosic and/or lignocellulosic material is wetted with a liquid, such as water.

In some embodiments, any processing described herein occurs after the cellulosic and/or lignocellulosic material remains dry as acquired or has been dried, e.g., using heat and/or reduced pressure. For example, in some embodiments, the cellulosic and/or lignocellulosic material has less than about five percent by weight retained water, measured at 25° C. and at fifty percent relative humidity.

If desired, a swelling agent, as defined herein, can be utilized in any process described herein. In some embodiments, when a cellulosic and/or lignocellulosic material is processed using radiation, less than about 25 percent by weight of the cellulosic and/or lignocellulosic material is in a swollen state, the swollen state being characterized as having a volume of more than about 2.5 percent higher than an unswollen state, e.g., more than 5.0, 7.5, 10, or 15 percent higher than the unswollen state. In some embodiments, when radiation is utilized on a cellulosic and/or lignocellulosic material, substantially none of the cellulosic and/or lignocellulosic material is in a swollen state.

In specific embodiments when radiation is utilized, the cellulosic and/or lignocellulosic material includes a swelling agent, and swollen cellulosic and/or lignocellulosic receives a dose of less than about 10 Mrad.

When radiation is utilized in any process, it can be applied while the cellulosic and/or lignocellulosic is exposed to air, oxygen-enriched air, or even oxygen itself, or blanketed by an inert gas such as nitrogen, argon, or helium. When maximum oxidation is desired, an oxidizing environment is utilized, such as air or oxygen.

When radiation is utilized, it may be applied to biomass, such as cellulosic and/or lignocellulosic material, under a pressure of greater than about 2.5 atmospheres, such as greater than 5, 10, 15, 20 or even greater than about 50 atmospheres.

In specific embodiments, the process includes irradiating and sonicating and irradiating precedes sonicating. In other specific embodiments, sonication precedes irradiating, or irradiating and sonicating occur concurrently.

In some embodiments, the process includes irradiating and sonicating (in either order or concurrently) and further includes oxidizing, pyrolyzing or steam exploding.

When the process includes radiation, the irradiating can be performed utilizing an ionizing radiation, such as gamma rays, x-rays, energetic ultraviolet radiation, such as ultraviolet C radiation having a wavelength of from about 100 nm to about 280 nm, a beam of particles, such as a beam of electrons, slow neutrons or alpha particles. In some embodiments, irradiating includes two or more radiation sources, such as gamma rays and a beam of electrons, which can be applied in either order or concurrently.

In specific embodiments, sonicating can performed at a frequency of between about 15 khz and about 25 khz, such as between about 18 khz and 22 khz utilizing a 1 KW or larger horn, e.g., a 2, 3, 4, 5, or even a 10 KW horn.

In some embodiments, the cellulosic and/or lignocellulosic material includes a first cellulose having a first number average molecular weight and the resulting carbohydrate includes a second cellulose having a second number average molecular weight lower than the first number average molecular weight. For example, the second number average molecular weight is lower than the first number average molecular weight by more than about twenty-five percent, e.g., 2×, 3×, 5×, 7×, 10×, 25×, even 100× reduction.

In some embodiments, the first cellulose has a first crystallinity and the second cellulose has a second crystallinity lower than the first crystallinity, such as lower than about two, three, five, ten, fifteen or twenty-five percent lower.

In some embodiments, the first cellulose has a first level of oxidation and the second cellulose has a second level of oxidation higher than the first level of oxidation, such as two, three, four, five, ten or even twenty-five percent higher.

Radiation Treatment

One or more irradiation processing sequences can be used to process raw feedstock from a wide variety of different sources to extract useful substances from the feedstock, and to provide partially degraded organic material which functions as input to further processing steps and/or sequences. Irradiation can reduce the molecular weight and/or crystallinity of feedstock. In some embodiments, energy deposited in a material that releases an electron from its atomic orbital is used to irradiate the materials. The radiation may be provided by 1) heavy charged particles, such as alpha particles, 2) electrons, produced, for example, in beta decay or electron beam accelerators, or 3) electromagnetic radiation, for example, gamma rays, x rays, or ultraviolet rays. In one approach, radiation produced by radioactive substances can be used to irradiate the feedstock. In another approach, electromagnetic radiation (e.g., produced using electron beam emitters) can be used to irradiate the feedstock. The doses applied depend on the desired effect and the particular feedstock. For example, high doses of radiation can break chemical bonds within feedstock components and low doses of radiation can increase chemical bonding (e.g., cross-linking) within feedstock components.

Figure 8:
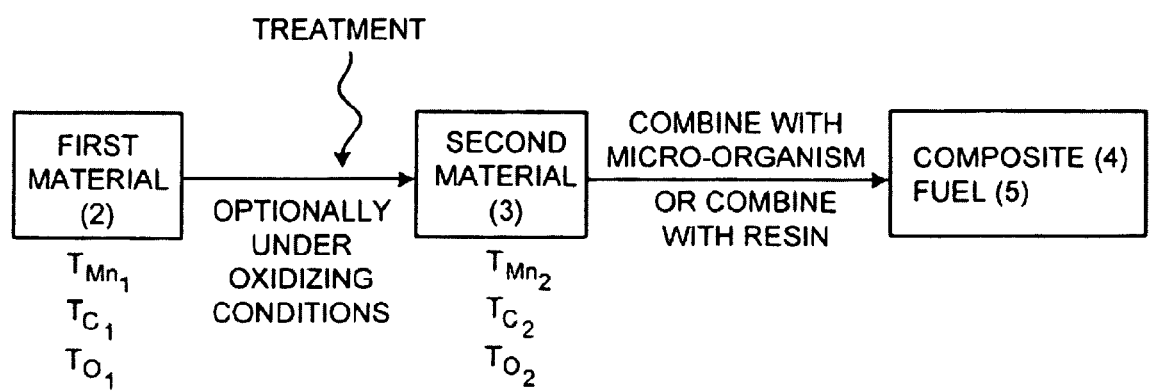
FIG. 8 is a block diagram illustrating a treatment sequence for processing feedstock.

Referring to FIG. 8, in one method, a first material 2 that is or includes cellulose having a first number average molecular weight ($^T M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material 3 that includes cellulose having a second number average molecular weight ($^T M_{N2}$) lower than the first number average molecular weight. The second material (or the first and second material) can be combined with a microorganism (e.g., a bacterium or a yeast) that can utilize the second and/or first material to produce a fuel 5 that is or includes hydrogen, an alcohol (e.g., ethanol or butanol, such as n-, sec- or t-butanol), an organic acid, a hydrocarbon or mixtures of any of these.

Since the second material 3 has cellulose having a reduced molecular weight relative to the first material, and in some instances, a reduced crystallinity as well, the second material is generally more dispersible, swellable and/or soluble in a solution containing a microorganism. These properties make the second material 3 more susceptible to chemical, enzymatic and/or biological attack relative to the first material 2, which can greatly improve the production rate and/or production level of a desired product, e.g., ethanol. Radiation can also sterilize the materials.

In some embodiments, the second number average molecular weight ($^T M_{N2}$) is lower than the first number average molecular weight ($^T M_{N1}$) by more than about 10 percent, e.g., 15, 20, 25, 30, 35, 40, 50 percent, 60 percent, or even more than about 75 percent.

In some instances, the second material has cellulose that has as crystallinity ($^T C_2$) that is lower than the crystallinity ($^T C_1$) of the cellulose of the first material. For example, ($^T C_2$) can be lower than ($^T C_1$) by more than about 10 percent, e.g., 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($^TO_2$) that is higher than the level of oxidation ($^TO_1$) of the first material. A higher level of oxidation of the material can aid in its dispersability, swellability and/or solubility, further enhancing the materials susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the biomass via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on its wavelength.

Figure 9:
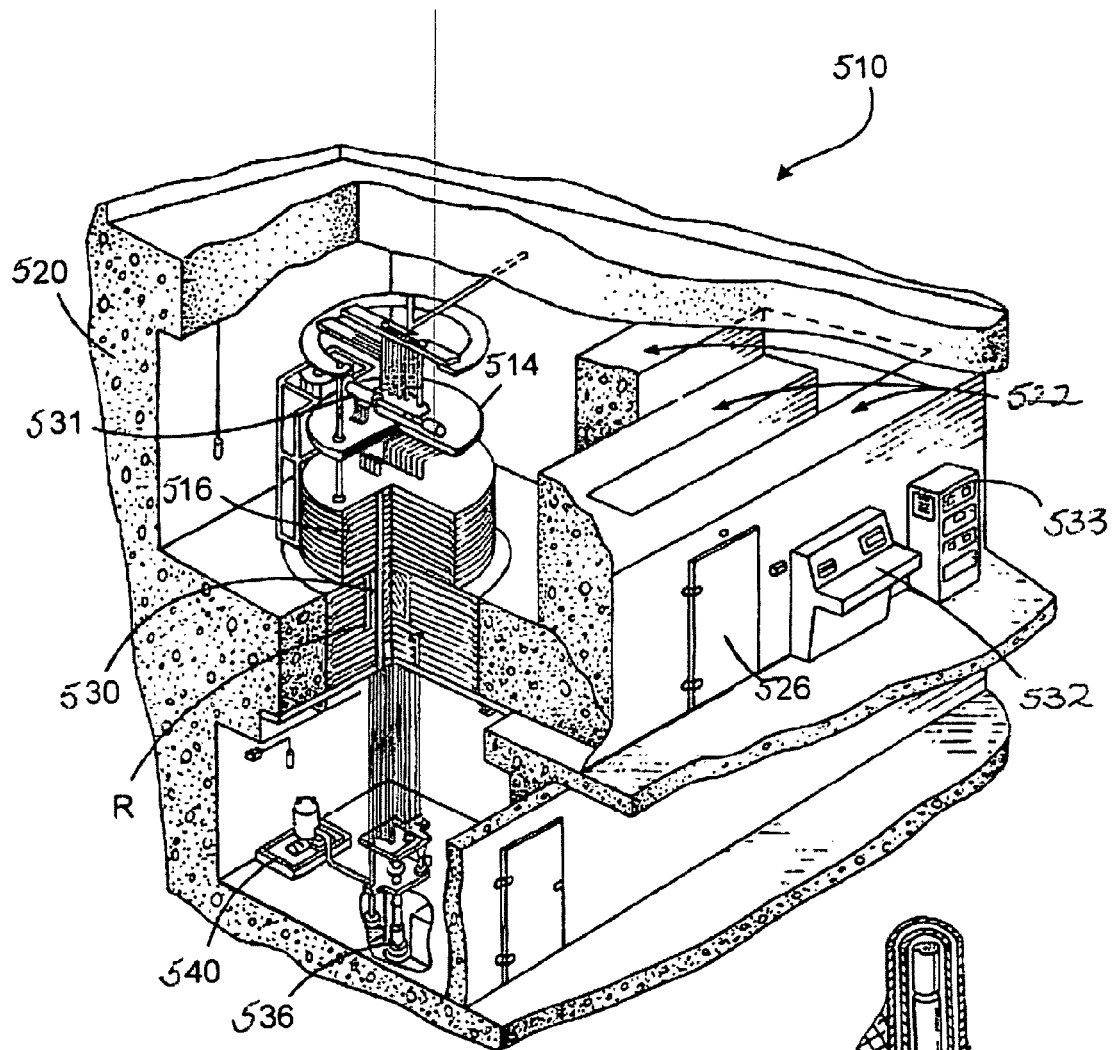
FIG. 9 is a perspective, cut-away view of a gamma irradiator.
Figure 10:
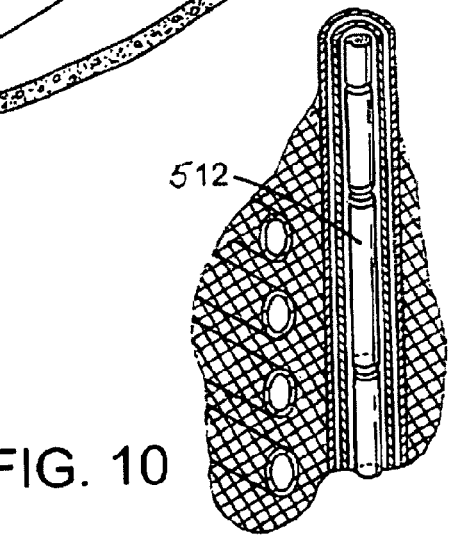
FIG. 10 is an enlarged perspective view of region R of FIG. 9.

For example, gamma radiation can be employed to irradiate the materials. Referring to FIGS. 9 and 10 (an enlarged view of region R), a gamma irradiator 510 includes gamma radiation sources 512, e.g., $^{60}$Co pellets, a working table 514 for holding the materials to be irradiated and storage 516, e.g., made of a plurality iron plates, all of which are housed in a concrete containment chamber 520 that includes a maze entranceway 522 beyond a lead-lined door 526. Storage 516 includes a plurality of channels 530, e.g., sixteen or more channels, allowing the gamma radiation sources to pass through storage on their way proximate the working table.

In operation, the sample to be irradiated is placed on a working table. The irradiator is configured to deliver the desired dose rate and monitoring equipment is connected to an experimental block 531. The operator then leaves the containment chamber, passing through the maze entranceway and through the lead-lined door. The operator mans a control panel 532, instructing a computer 533 to lift the radiation sources 512 into working position using cylinder 536 attached to a hydraulic pump 540.

Gamma radiation has the advantage of a significant penetration depth into a variety of material in the sample. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Electron Beam

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Figure 11:
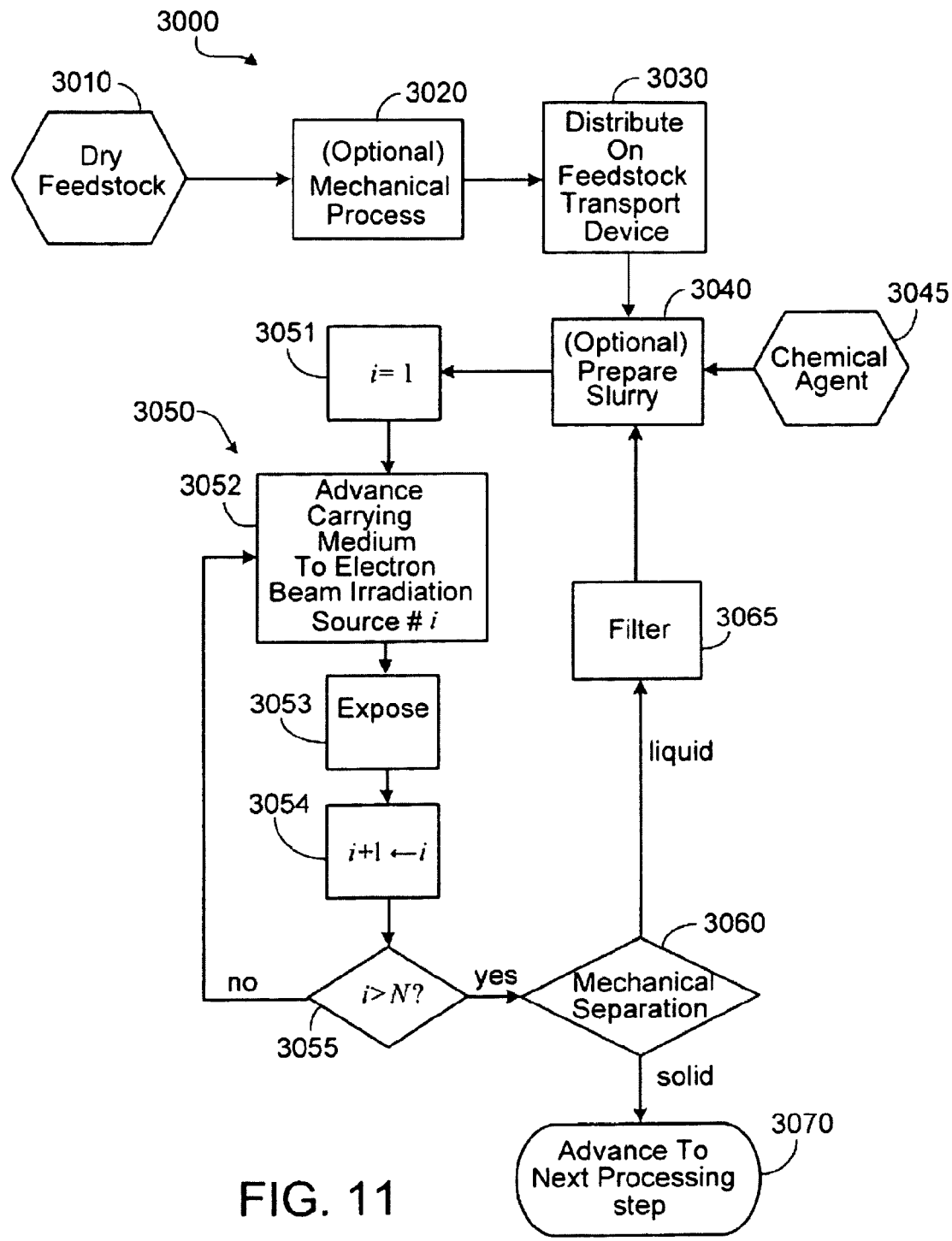
FIG. 11 is a block diagram illustrating an electron beam irradiation feedstock pretreatment sequence.
Figure 12:
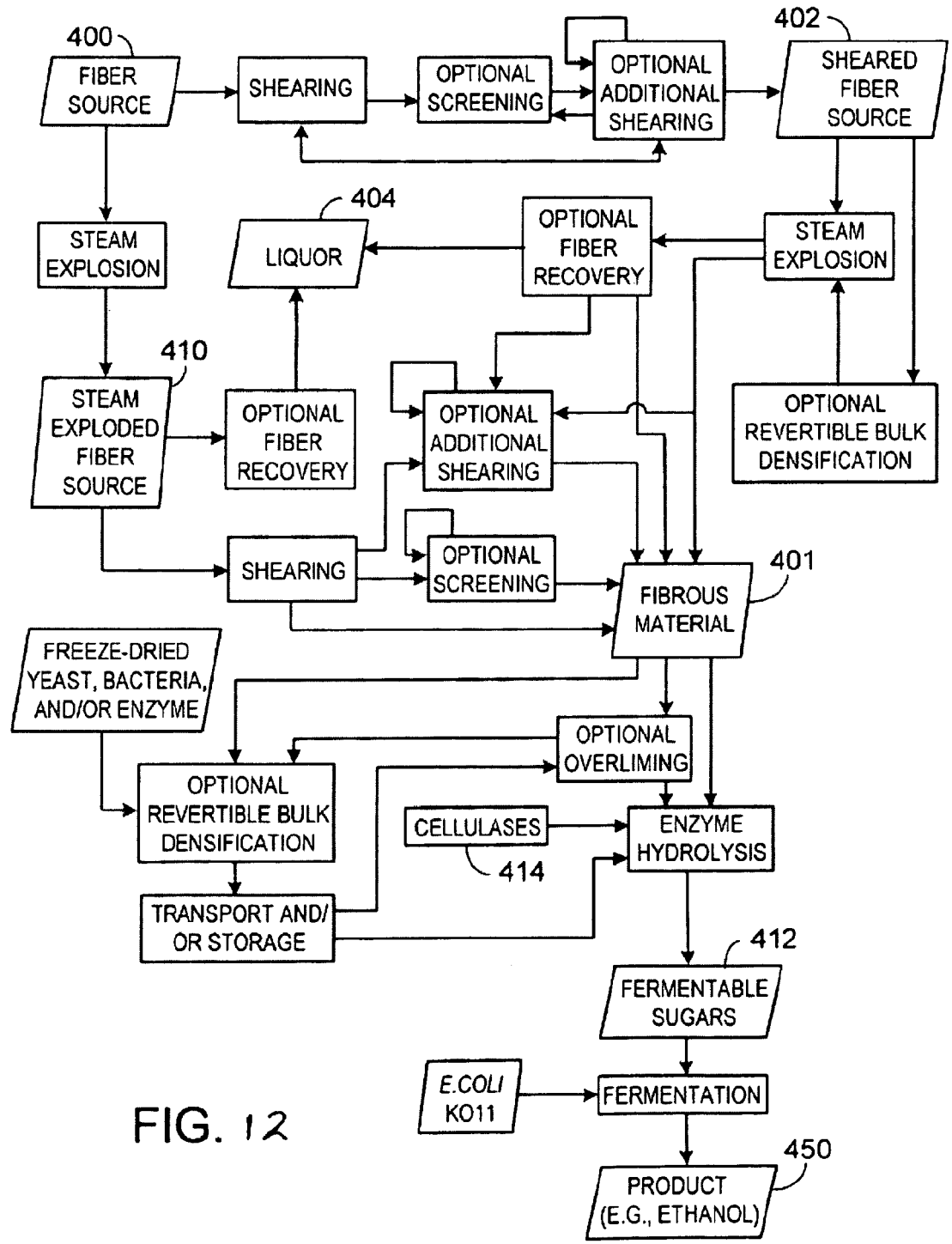
FIG. 12 is block diagram illustrating a general overview of the process of converting a fiber source into a product, e.g., ethanol.

FIG. 11 shows a process flow diagram 3000 that includes various steps in an electron beam irradiation feedstock pretreatment sequence. In first step 3010, a supply of dry feedstock is received from a feed source. As discussed above, the dry feedstock from the feed source may be pre-processed prior to delivery to the electron beam irradiation devices. For example, if the feedstock is derived from plant sources, certain portions of the plant material may be removed prior to collection of the plant material and/or before the plant material is delivered by the feedstock transport device. Alternatively, or in addition, as expressed in optional step 3020, the biomass feedstock can be subjected to mechanical processing (e.g., to reduce the average length of fibers in the feedstock) prior to delivery to the electron beam irradiation devices.

In step 3030, the dry feedstock is transferred to a feedstock transport device (e.g., a conveyor belt) and is distributed over the cross-sectional width of the feedstock transport device approximately uniformly by volume. This can be accomplished, for example, manually or by inducing a localized vibration motion at some point in the feedstock transport device prior to the electron beam irradiation processing.

In some embodiments, a mixing system introduces a chemical agent 3045 into the feedstock in an optional process 3040 that produces a slurry. Combining water with the processed feedstock in mixing step 3040 creates an aqueous feedstock slurry that may be transported through, for example, piping rather than using, for example, a conveyor belt.

The next step 3050 is a loop that encompasses exposing the feedstock (in dry or slurry form) to electron beam radiation via one or more (say, N) electron beam irradiation devices. The feedstock slurry is moved through each of the N "showers" of electron beams at step 3052. The movement may either be at a continuous speed through and between the showers, or there may be a pause through each shower, followed by a sudden movement to the next shower. A small slice of the feedstock slurry is exposed to each shower for some predetermined exposure time at step 3053.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. Effectiveness of depolymerization of the feedstock slurry depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Tradeoffs in considering electron energies include energy costs; here, a lower electron energy may be advantageous in encouraging depolymerization of certain feedstock slurry (see, for example, Bouchard, et al, Cellulose (2006) 13: 601-610).

It may be advantageous to provide a double-pass of electron beam irradiation in order to provide a more effective depolymerization process. For example, the feedstock transport device could direct the feedstock (in dry or slurry form) underneath and in a reverse direction to its initial transport direction. Double-pass systems can allow thicker feedstock slurries to be processed and can provide a more uniform depolymerization through the thickness of the feedstock slurry.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available.

Once a portion of feedstock slurry has been transported through the N electron beam irradiation devices, it may be necessary in some embodiments, as in step 3060, to mechanically separate the liquid and solid components of the feedstock slurry. In these embodiments, a liquid portion of the feedstock slurry is filtered for residual solid particles and recycled back to the slurry preparation step 3040. A solid portion of the feedstock slurry is then advanced on to the next processing step 3070 via the feedstock transport device. In other embodiments, the feedstock is maintained in slurry form for further processing.

Particles Heavier than Electrons
Ion Particle Beams

Particles heavier than electrons can be utilized to irradiate carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phoshorus ions, oxygen ions or nitrogen ions can be utilized. In some embodiments, particles heavier than electrons can induce higher amounts of chain scission. In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In this section, the types and properties of particles that can be used to irradiate various types of biomass materials are disclosed. Further, systems and methods for producing beams of such particles are disclosed.

1. Types of Ions

In general, many different types of ions can be used to irradiate biomass materials. For example, in some embodiments, ion beams can include relatively light ions, such as protons and/or helium ions. In certain embodiments, the ion beams can include moderately heavier ions, such as carbon ions, nitrogen ions, oxygen ions, and/or neon ions. In some embodiments, ion beams can include still heavier ions, such as argon ions, silicon ions, phosphorus ions, sodium ions, calcium ions, and/or iron ions.

In certain embodiments, ion beams used to irradiate biomass materials can include more than one different type of ions. For example, ion beams can include mixtures of two or more (e.g., three, or four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam, where each of the different types of ions has different effectiveness in irradiating biomass materials.

In some embodiments, ion beams for irradiating biomass materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to biomass materials, initiating and sustaining cationic ring-opening chain scission reactions in an oxidative environment.

In certain embodiments, ion beams for irradiating biomass materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to biomass materials, causing anionic ring-opening chain scission reactions in a reducing environment.

In some embodiments, beams for irradiating biomass materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

The preceding discussion has focused on ion beams that include mononuclear ions and/or neutral particles (e.g., atomic ions and neutral atoms). Typically, such particles are the easiest—in energetic terms—to generate, and parent particles from which these species are generated may be available in abundant supply. However, in some embodiments, beams for irradiating biomass materials can include one or more types of ions or neutral particles that are polynuclear, e.g., including two or more different types of nuclei. For example, ion beams can include positive and/or negative ions and/or neutral particles formed from species such as $N_2$, $O_2$, $H_2$, $CH_4$, and other molecular species. Ion beams can also include ions and/or neutral particles formed from heavier species that include even more nuclei, such as various hydrocarbon-based species and/or various inorganic species, including coordination compounds of various metals.

In certain embodiments, ion beams used to irradiate biomass materials include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Doses

In some embodiments, the irradiating (with any radiation source or a combination of sources) is performed until the material receives a dose of at least 0.25 Mrad, e.g., at least 1.0 Mrad, at least 2.5 Mrad, at least 5.0 Mrad, or at least 10.0 Mrad. In some embodiments, the irradiating is performed until the material receives a dose of between 1.0 Mrad and 6.0 Mrad, e.g., between 1.5 Mrad and 4.0 Mrad. In some embodiments, the irradiating is performed until the material receives a dose of at least 25, 50, 75, 100, 125, 150, 175, or even greater than 200 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours. In some embodiments, the irradiating is performed at a dose rate of between 5.0 and 150.0 kilorads/hour, e.g., between 10.0 and 125.0 kilorads/hour or between 15.0 and 75.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Sonication

One or more sonication processing sequences can be used to process raw feedstock from a wide variety of different sources to extract useful substances from the feedstock, and to provide partially degraded organic material which functions as input to further processing steps and/or sequences. Sonication can reduce the molecular weight and/or crystallinity of feedstock.

Referring again to FIG. 8, in one method, a first material 2 that includes cellulose having a first number average molecular weight ($^T M_{N1}$) is dispersed in a medium, such as water, and sonicated and/or otherwise cavitated, to provide a second material 3 that includes cellulose having a second number average molecular weight ($^T M_{N2}$) lower than the first number average molecular weight. The second material (or the first and second material in certain embodiments) can be combined with a microorganism (e.g., a bacterium or a yeast) that can utilize the second and/or first material to produce a fuel 5 that is or includes hydrogen, an alcohol, an organic acid, a hydrocarbon or mixtures of any of these.

Since the second material has cellulose having a reduced molecular weight relative to the first material, and in some instances, a reduced crystallinity as well, the second material is generally more dispersible, swellable, and/or soluble in a solution containing the microorganism, e.g., at a concentration of greater than $10^6$ microorganisms/mL. These properties make the second material 3 more susceptible to chemical, enzymatic, and/or microbial attack relative to the first material 2, which can greatly improve the production rate and/or production level of a desired product, e.g., ethanol. Sonication can also sterilize the materials, but should not be used while the microorganisms are supposed to be alive.

In some embodiments, the second number average molecular weight ($^T M_{N2}$) is lower than the first number average molecular weight NO by more than about 10 percent, e.g., 15, 20, 25, 30, 35, 40, 50 percent, 60 percent, or even more than about 75 percent.

In some instances, the second material has cellulose that has as crystallinity ($^T C_2$) that is lower than the crystallinity ($^T C_1$) of the cellulose of the first material. For example, ($^T C_2$) can be lower than ($^T C_1$) by more than about 10 percent, e.g., 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($^T O_2$) that is higher than the level of oxidation ($^T O_1$) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process raw feedstock from a wide variety of different sources to extract useful substances from the feedstock, and to provide partially degraded (functionalized) organic material which functions as input to further processing steps and/or sequences. Pyrolysis could be performed before, during (in a dry zone), or after the screw extrusion process.

Referring again to the general schematic in FIG. 8, a first material 2 that includes cellulose having a first number average molecular weight ($^{T}M_{N1}$) is pyrolyzed, e.g., by heating the first material in a tube furnace, to provide a second material 3 that includes cellulose having a second number average molecular weight ($^{T}M_{N2}$) lower than the first number average molecular weight. The second material (or the first and second material in certain embodiments) is/are combined with a microorganism (e.g., a bacterium or a yeast) that can utilize the second and/or first material to produce a fuel 5 that is or includes hydrogen, an alcohol (e.g., ethanol or butanol, such as n-, sec or t-butanol), an organic acid, a hydrocarbon or mixtures of any of these.

Since the second material has cellulose having a reduced molecular weight relative to the first material, and in some instances, a reduced crystallinity as well, the second material is generally more dispersible, swellable and/or soluble in a solution containing the microorganism, e.g., at a concentration of greater than $10^6$ microorganisms/mL. These properties make the second material 3 more susceptible to chemical, enzymatic and/or microbial attack relative to the first material 2, which can greatly improve the production rate and/or production level of a desired product, e.g., ethanol. Pyrolysis can also sterilize the first and second materials.

In some embodiments, the second number average molecular weight ($^{T}M_{N2}$) is lower than the first number average molecular weight NO by more than about 10 percent, e.g., 15, 20, 25, 30, 35, 40, 50 percent, 60 percent, or even more than about 75 percent.

In some instances, the second material has cellulose that has as crystallinity ($^{T}C_2$) that is lower than the crystallinity ($^{T}C_1$) of the cellulose of the first material. For example, ($^{T}C_2$) can be lower than ($^{T}C_1$) by more than about 10 percent, e.g., 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($^{T}O_2$) that is higher than the level of oxidation ($^{T}O_1$) of the first material. A higher level of oxidation of the material can aid in its dispersability, swellability and/or solubility, further enhancing the materials susceptibility to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, which can increase its hydrophilicity.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process raw feedstock from a wide variety of different sources to extract useful substances from the feedstock, and to provide partially degraded organic material which functions as input to further processing steps and/or sequences. Oxidation may be performed before, during, or after screw extrusion. For example, during extrusion oxidation can occur by injecting an oxidant, e.g. ammonium persulfate or sodium hypochlorite, into the biomass while the biomass is in the extruder.

Referring again to FIG. 8, a first material (2) that includes cellulose having a first number average molecular weight ($^{T}M_{N1}$) and having a first oxygen content ($^{T}O_1$) is oxidized, e.g., by heating the first material in a tube furnace in stream of air or oxygen-enriched air, to provide a second material (3) that includes cellulose having a second number average molecular weight ($^{T}M_{N2}$) and having a second oxygen content ($^{T}O_2$) higher than the first oxygen content ($^{T}O_1$).

Such materials can also be combined with a solid and/or a liquid. For example, the liquid can be in the form of a solution and the solid can be particulate in form. The liquid and/or solid can include a microorganism, e.g., a bacterium, and/or an enzyme. For example, the bacterium and/or enzyme can work on the cellulosic or lignocellulosic material to produce a fuel, such as ethanol, or a coproduct, such as a protein. Fuels and coproducts are described in FIBROUS MATERIALS AND COMPOSITES," U.S. Ser. No. 11/453,951, filed Jun. 15, 2006. The entire contents of each of the foregoing applications are incorporated herein by reference.

In some embodiments in which the materials are used to make a fuel or a coproduct, the starting number average molecular weight (prior to oxidation) is from about 200,000 to about 3,200,000, e.g., from about 250,000 to about 1,000, 000 or from about 250,000 to about 700,000, and the number average molecular weight after oxidation is from about 50,000 to about 200,000, e.g., from about 60,000 to about 150,000 or from about 70,000 to about 125,000. However, in some embodiments, e.g., after extensive oxidation, it is possible to have a number average molecular weight of less than about 10,000 or even less than about 5,000.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the oxygen content of the first material. Oxygen content is measured by elemental analysis by pyrolyzing a sample in a furnace operating 1300° C. or higher. A suitable elemental analyzer is the LECO CHNS-932 analyzer with a VTF-900 high temperature pyrolysis furnace.

In some embodiments, oxidation of first material 200 does not result in a substantial change in the crystallinity of the cellulose. However, in some instances, e.g., after extreme oxidation, the second material has cellulose that has as crystallinity ($^TC_2$) that is lower than the crystallinity ($^TC_1$) of the cellulose of the first material. For example, ($^TC_2$) can be lower than ($^TC_1$) by more than about 5 percent, e.g., 10, 15, 20, or even 25 percent. This can be desirable when optimizing the flexural fatigue properties of the composite is a goal. For example, reducing the crystallinity can improve the elongation at break or can enhance the impact resistance of a composite. This can also be desirable to enhance solubility of the materials in a liquid, such as a liquid that includes a bacterium and/or an enzyme.

Generally, oxidation of first material 200 occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Other Processes

Steam explosion can be used alone without any of the processes described herein, or in combination with any of the processes described herein. In some cases, steam under pressure can be introduced into the screw extruder during a screw extrusion step.

FIG. 23 shows an overview of the entire process of converting a fiber source 400 into a product 450, such as ethanol, by a process that includes shearing and steam explosion to produce a fibrous material 401, which is then hydrolyzed and converted, e.g., fermented, to produce the product. The fiber source can be transformed into the fibrous material 401 through a number of possible methods, including at least one shearing process and at least one steam explosion process.

For example, one option includes shearing the fiber source, followed by optional screening step(s) and optional additional shearing step(s) to produce a sheared fiber source 402, which can then be steam exploded to produce the fibrous material 401. The steam explosion process is optionally followed by a fiber recovery process to remove liquids or the "liquor" 404, resulting from the steam exploding process. The material resulting from steam exploding the sheared fiber source may be further sheared by optional additional shearing step(s) and/or optional screening step(s).

In another method, the fibrous material 401 is first steam exploded to produce a steam exploded fiber source 410. The resulting steam exploded fiber source is then subjected to an optional fiber recovery process to remove liquids, or the liquor. The resulting steam exploded fiber source can then be sheared to produce the fibrous material. The steam exploded fiber source can also be subject to one or more optional screening steps and/or one or more optional additional shearing steps. The process of shearing and steam exploding the fiber source to produce the sheared and steam exploded fibrous material will be further discussed below.

The fiber source can be cut into pieces or strips of confetti material prior to shearing or steam explosion. The shearing processes can take place in a dry (e.g., having less than 0.25 percent by weight absorbed water), hydrated, or even while the material is partially or fully submerged in a liquid, such as water or isopropanol. The process can also optimally include steps of drying the output after steam exploding or shearing to allow for additional steps of dry shearing or steam exploding. The steps of shearing, screening, and steam explosion can take place with or without the presence of various chemical solutions.

In a steam explosion process, the fiber source or the sheared fiber source is contacted with steam under high pressure, and the steam diffuses into the structures of the fiber source (e.g., the lignocellulosic structures). The steam then condenses under high pressure thereby "wetting" the fiber source. The moisture in the fiber source can hydrolyze any acetyl groups in the fiber source (e.g., the acetyl groups in the hemicellulose fractions), forming organic acids such as acetic and uronic acids. The acids, in turn, can catalyze the depolymerization of hemicellulose, releasing xylan and limited amounts of glucan. The "wet" fiber source (or sheared fiber source, etc.) is then "exploded" when the pressure is released. The condensed moisture instantaneously evaporates due to the sudden decrease in pressure and the expansion of the water vapor exerts a shear force upon the fiber source (or sheared fiber source, etc.). A sufficient shear force will cause the mechanical breakdown of the internal structures (e.g., the ligocellulosic structures) of the fiber source.

The sheared and steam exploded fibrous material is then converted into a useful product, such as ethanol. In some embodiments, the fibrous material is converted into a fuel. One method of converting the fibrous material into a fuel is by hydrolysis to produce fermentable sugars, 412, which are then fermented to produce the product. Other known and unknown methods of converting fibrous materials into fuels may also be used.

In some embodiments, prior to combining the microorganism, the sheared and steam exploded fibrous material 401 is sterilized to kill any competing microorganisms that may be on the fibrous material. For example, the fibrous material can be sterilized by exposing the fibrous material to radiation, such as infrared radiation, ultraviolet radiation, or an ionizing radiation, such as gamma radiation. The microorganisms can also be killed using chemical sterilants, such as bleach (e.g., sodium hypochlorite), chlorhexidine, or ethylene oxide.

One method to hydrolyze the sheared and steam exploded fibrous material is by the use of cellulases. Cellulases are a group of enzymes that act synergistically to hydrolyze cellulose. Commercially available Accellerase3 1000, which contains a complex of enzymes that reduces lignocellulosic biomass into fermentable sugars can also be used.

According to current understanding, the components of cellulase include endoglucanases, exoglucanases (cellobiohydrolases), and b-glucosidases (cellobiases). Synergism between the cellulase components exists when hydrolysis by a combination of two or more components exceeds the sum of the activities expressed by the individual components. The generally accepted mechanism of a cellulase system (particularly of *T. longibrachiatum*) on crystalline cellulose is: endoglucanase hydrolyzes internal β-1,4-glycosidic bonds of the amorphous regions, thereby increasing the number of exposed non-reducing ends. Exoglucanases then cleave off cellobiose units from the nonreducing ends, which in turn are hydrolyzed to individual glucose units by b-glucosidases. There are several configurations of both endo- and exo-glucanases differing in stereospecificities. In general, the synergistic action of the components in various configurations is required for optimum cellulose hydrolysis. Cellulases, however, are more inclined to hydrolyze the amorphous regions of cellulose. A linear relationship between crystallinity and hydrolysis rates exists whereby higher crystallinity indices correspond to slower enzyme hydrolysis rates. Amorphous regions of cellulose hydrolyze at twice the rate of crystalline regions. The hydrolysis of the sheared and steam exploded fibrous material may be performed by any hydrolyzing biomass process.

Steam explosion of biomass sometimes causes the formation of by-products, e.g., toxicants, that are inhibitory to microbial and enzymatic activities. The process of converting the sheared and steam exploded fibrous material into a fuel can therefore optionally include an overliming step prior to fermentation to precipitate some of the toxicants. For example, the pH of the sheared and steam exploded fibrous material may be raised to exceed the pH of 10 by adding calcium hydroxide ($Ca(OH)_2$) followed by a step of lowering the pH to about 5 by adding $H_2SO_4$. The overlimed fibrous material may then be used as is without the removal of precipitates. As shown in FIG. 23, the optional overliming step occurs just prior to the step of hydrolysis of the sheared and steam exploded fibrous material, but it is also contemplated to perform the overliming step after the hydrolysis step and prior to the fermenting step.

Primary Processes

Fermentation

Generally, various microorganisms can produce a number of useful products, such as a fuel, by operating on, e.g., fermenting the pretreated biomass materials. For example, alcohols, organic acids, hydrocarbons, hydrogen, proteins or mixtures of any of these materials can be produced by fermentation or other processes.

The microorganism can be a natural microorganism or an engineered microorganism. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

To aid in the breakdown of the materials that include the cellulose, one or more enzymes, e.g., a cellulolytic enzyme can be utilized. In some embodiments, the materials that include the cellulose are first treated with the enzyme, e.g., by combining the material and the enzyme in an aqueous solution. This material can then be combined with the microorganism. In other embodiments, the materials that include the cellulose, the one or more enzymes and the microorganism are combined at the concurrently, e.g., by combining in an aqueous solution.

Also, to aid in the breakdown of the materials that include the cellulose, the materials can be treated post irradiation with heat, a chemical (e.g., mineral acid, base or a strong oxidizer such as sodium hypochlorite), and/or an enzyme.

During the fermentation, sugars released from cellulolytic hydrolysis or the saccharification step, are fermented to, e.g., ethanol, by a fermenting microorganism such as yeast. Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus*, *Saccharomyces uvarum*; the genus *Kluyveromyces*, e.g., species *Kluyveromyces marxianus*, *Kluyveromyces fragilis*; the genus *Candida*, e.g., *Candida pseudotropicalis*, and *Candida brassicae*, the genus *Clavispora*, e.g., species *Clavispora lusitaniae* and *Clavispora opuntiae* the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212). In a particular embodiment, the microorganism may be *pichia stipitis* (NRRL-7124).

Commercially available yeast include, for example, Red Star®/Lesaffre Ethanol Red (available from Red Star/Lesaffre, USA) FALI® (available from Fleischmann's Yeast, a division of Burns Philip Food Inc., USA), SUPERSTART® (available from Alltech), GERT STRAND® (available from Gert Strand AB, Sweden) and FERMOL® (available from DSM Specialties).

Bacteria that can ferment biomass to ethanol and other products include, e.g., *Zymomonas mobilis* and *Clostridium thermocellum* (Philippidis, 1996, supra). Leschine et al. (*International Journal of Systematic and Evolutionary Microbiology* 2002, 52, 1155-1160) isolated an anaerobic, mesophilic, cellulolytic bacterium from forest soil, *Clostridium phytofermentans* sp. nov., which converts cellulose to ethanol.

Fermentation of biomass to ethanol and other products may be carried out using certain types of thermophilic or genetically engineered microorganisms, such *Thermoanaerobacter* species, including *T. mathranii*, and yeast species such as *Pichia* species. An example of a strain of *T. mathranii* is A3M4 described in Sonne-Hansen et al. (*Applied Microbiology and Biotechnology* 1993, 38, 537-541) or Ahring et al. (*Arch. Microbiol.* 1997, 168, 114-119).

Yeast and *Zymomonas* bacteria can be used for fermentation or conversion. The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Enzymes which break down biomass, such as cellulose, to lower molecular weight carbohydrate-containing materials, such as glucose, during saccharification are referred to as cellulolytic enzymes or cellulase. These enzymes may be a complex of enzymes that act synergistically to degrade crystalline cellulose. Examples of cellulolytic enzymes include: endoglucanases, cellobiohydrolases, and cellobiases (☺-glucosidases). A cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble ☺-1,4-linked dimer of glucose. Finally cellobiase cleaves cellobiose to yield glucose.

A cellulase is capable of degrading biomass and may be of fungal or bacterial origin. Suitable enzymes include cellulases from the genera *Bacillus*, *Pseudomonas*, *Humicola*, *Fusarium*, *Thielavia*, *Acremonium*, *Chrysosporium* and *Trichoderma*, and include species of *Humicola*, *Coprinus*, *Thielavia*, *Fusarium*, *Myceliophthora*, *Acremonium*, *Cephalosporium*, *Scytalidium*, *Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus*, *Fusarium oxysporum*, *Myceliophthora*

*thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Anaerobic cellulolytic bacteria have also been isolated from soil, e.g., a novel cellulolytic species of *Clostiridium, Clostridium phytofermentans* sp. nov. (see Leschine et. al, *International Journal of Systematic and Evolutionary Microbiology* (2002), 52, 1155-1160).

Cellulolytic enzymes using recombinant technology can also be used (see, e.g., WO 2007/071818 and WO 2006/110891).

The cellulolytic enzymes used can be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi, Academic Press*, CA 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., *Biochemical Engineering Fundamentals*, McGraw-Hill Book Company, NY, 1986).

Treatment of cellulose with cellulase is usually carried out at temperatures between 30° C. and 65° C. Cellulases are active over a range of pH of about 3 to 7. A saccharification step may last up to 120 hours. The cellulase enzyme dosage achieves a sufficiently high level of cellulose conversion. For example, an appropriate cellulase dosage is typically between 5.0 and 50 Filter Paper Units (FPU or IU) per gram of cellulose. The FPU is a standard measurement and is defined and measured according to Ghose (1987, Pure and Appl. Chem. 59:257-268).

Gasification

In addition to using pyrolysis for pre-treatment of feedstock, pyrolysis can also be used to process pre-treated feedstock to extract useful materials. In particular, a form of pyrolysis known as gasification can be employed to generate fuel gases along with various other gaseous, liquid, and solid products. To perform gasification, the pre-treated feedstock is introduced into a pyrolysis chamber and heated to a high temperature, typically 700° C. or more. The temperature used depends upon a number of factors, including the nature of the feedstock and the desired products.

Quantities of oxygen (e.g., as pure oxygen gas and/or as air) and steam (e.g., superheated steam) are also added to the pyrolysis chamber to facilitate gasification. These compounds react with carbon-containing feedstock material in a multiple-step reaction to generate a gas mixture called synthesis gas (or "syngas"). Essentially, during gasification, a limited amount of oxygen is introduced into the pyrolysis chamber to allow some feedstock material to combust to form carbon monoxide and generate process heat. The process heat can then be used to promote a second reaction that converts additional feedstock material to hydrogen and carbon monoxide.

In a first step of the overall reaction, heating the feedstock material produces a char that can include a wide variety of different hydrocarbon-based species. Certain volatile materials can be produced (e.g., certain gaseous hydrocarbon materials), resulting in a reduction of the overall weight of the feedstock material. Then, in a second step of the reaction, some of the volatile material that is produced in the first step reacts with oxygen in a combustion reaction to produce both carbon monoxide and carbon dioxide. The combustion reaction releases heat, which promotes the third step of the reaction. In the third step, carbon dioxide and steam (e.g., water) react with the char generated in the first step to form carbon monoxide and hydrogen gas. Carbon monoxide can also react with steam, in a water gas shift reaction, to form carbon dioxide and further hydrogen gas.

Gasification can be used as a primary process to generate products directly from pre-treated feedstock for subsequent transport and/or sale, for example. Alternatively, or in addition, gasification can be used as an auxiliary process for generating fuel for an overall processing system. The hydrogen-rich syngas that is generated via the gasification process can be burned, for example, to generate electricity and/or process heat that can be directed for use at other locations in the processing system. As a result, the overall processing system can be at least partially self-sustaining. A number of other products, including pyrolysis oils and gaseous hydrocarbon-based substances, can also be obtained during and/or following gasification; these can be separated and stored or transported as desired.

A variety of different pyrolysis chambers are suitable for gasification of pre-treated feedstock, including the pyrolysis chambers disclosed herein. In particular, fluidized bed reactor systems, in which the pre-treated feedstock is fluidized in steam and oxygen/air, provide relatively high throughput and straightforward recovery of products. Solid char that remains following gasification in a fluidized bed system (or in other pyrolysis chambers) can be burned to generate additional process heat to promote subsequent gasification reactions.

Post-Processing

Distillation

After fermentation, the resulting fluids can be distilled using, for example, a "beer column" to separate ethanol and other alcohols from the majority of water and residual solids. The vapor exiting the beer column can be 35% by weight ethanol and fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Waste Water Treatment

Wastewater treatment is used to minimize makeup water requirements of the plant by treating process water for reuse within the plant. Wastewater treatment can also produce fuel (e.g., sludge and biogas) that can be used to improve the overall efficiency of the ethanol production process. For example, as described in further detail below, sludge and biogas can be used to create steam and electricity that can be used in various plant processes.

Wastewater is initially pumped through a screen (e.g., a bar screen) to remove large particles, which are collected in a hopper. In some embodiments, the large particles are sent to a landfill. Additionally or alternatively, the large particles are burned to create steam and/or electricity as described in further detail below. In general, the spacing on the bar screen is between ¼ inch to 1 inch spacing (e.g., ½ inch spacing).

The wastewater then flows to an equalization tank, where the organic concentration of the wastewater is equalized during a retention time. In general, the retention time is between 8 hours and 36 hours (e.g., 24 hours). A mixer is disposed within the tank to stir the contents of the tank. In some embodiments, a plurality of mixers disposed throughout the tank are used to stir the contents of the tank. In certain embodiments, the mixer substantially mixes the contents of the equalization tank such that conditions (e.g., wastewater concentration and temperature) throughout the tank are uniform.

A first pump moves water from the equalization tank through a liquid-to-liquid heat exchanger. The heat exchanger is controlled (e.g., by controlling the flow rate of fluid through the heat exchanger) such that wastewater exiting the heat exchanger is at a desired temperature for anaerobic treatment. For example, the desired temperature for anaerobic treatment can be between 40° C. to 60° C.

After exiting the heat exchanger, the wastewater enters one or more anaerobic reactors. In some embodiments, the concentration of sludge in each anaerobic reactor is the same as the overall concentration of sludge in the wastewater. In other embodiments, the anaerobic reactor has a higher concentration of sludge than the overall concentration of sludge in the wastewater.

A nutrient solution containing nitrogen and phosphorus is metered into each anaerobic reactor containing wastewater. The nutrient solution reacts with the sludge in the anaerobic reactor to produce biogas which can contain 50% methane and have a heating value of approximately 12,000 British thermal units, or Btu, per pound). The biogas exits each anaerobic reactor through a vent and flows into a manifold, where a plurality of biogas streams are combined into a single stream. A compressor moves the stream of biogas to a boiler or a combustion engine as described in further detail below. In some embodiments, the compressor also moves the single stream of biogas through a desulphurization catalyst. Additionally or alternatively, the compressor can move the single stream of biogas through a sediment trap.

A second pump moves anaerobic effluent from the anaerobic reactors to one or more aerobic reactors (e.g., activated sludge reactors). An aerator is disposed within each aerobic reactor to mix the anaerobic effluent, sludge, oxygen (e.g., oxygen contained in air). Within each aerobic reactor, oxidation of cellular material in the anaerobic effluent produces carbon dioxide, water, and ammonia.

Aerobic effluent moves (e.g., via gravity) to a separator, where sludge is separated from treated water. Some of the sludge is returned to the one or more aerobic reactors to create an elevated sludge concentration in the aerobic reactors, thereby facilitating the aerobic breakdown of cellular material in the wastewater. A conveyor removes excess sludge from the separator. As described in further detail below, the excess sludge is used as fuel to create steam and/or electricity.

The treated water is pumped from the separator to a settling tank. Solids dispersed throughout the treated water settle to the bottom of the settling tank and are subsequently removed. After a settling period, treated water is pumped from the settling tank through a fine filter to remove any additional solids remaining in the water. In some embodiments, chlorine is added to the treated water to kill pathogenic bacteria. In some embodiments, one or more physical-chemical separation techniques are used to further purify the treated water. For example, treated water can be pumped through a carbon adsorption reactor. As another example, treated water can pumped through a reverse osmosis reactor.

Waste Combustion

The production of alcohol from biomass can result in the production of various by-product streams useful for generating steam and electricity to be used in other parts of the plant. For example, steam generated from burning by-product streams can be used in the distillation process. As another example, electricity generated from burning by-product streams can be used to power electron beam generators and ultrasonic transducers used in pretreatment.

The by-products used to generate steam and electricity are derived from a number of sources throughout the process. For example, anaerobic digestion of wastewater produces a biogas high in methane and a small amount of waste biomass (sludge). As another example, post-distillate solids (e.g., unconverted lignin, cellulose, and hemicellulose remaining from the pretreatment and primary processes) can be used as a fuel.

The biogas is diverted to a combustion engine connected to an electric generator to produce electricity. For example, the biogas can be used as a fuel source for a spark-ignited natural gas engine. As another example, the biogas can be used as a fuel source for a direct-injection natural gas engine. As another example, the biogas can be used as a fuel source for a combustion turbine. Additionally or alternatively, the combustion engine can be configured in a cogeneration configuration. For example, waste heat from the combustion engines can be used to provide hot water or steam throughout the plant.

The sludge, and post-distillate solids are burned to heat water flowing through a heat exchanger. In some embodiments, the water flowing through the heat exchanger is evaporated and superheated to steam. In certain embodiments, the steam is used in the pretreatment rector and in heat exchange in the distillation and evaporation processes. Additionally or alternatively, the steam expands to power a multi-stage steam turbine connected to an electric generator. Steam exiting the steam turbine is condensed with cooling water and returned to the heat exchanger for reheating to steam. In some embodiments, the flow rate of water through the heat exchanger is controlled to obtain a target electricity output from the steam turbine connected to an electric generator. For example, water can be added to the heat exchanger to ensure that the steam turbine is operating above a threshold condition (e.g., the turbine is spinning fast enough to turn the electric generator).

While certain embodiments have been described, other embodiments are possible.

As an example, while the biogas is described as being diverted to a combustion engine connected to an electric generator, in certain embodiments, the biogas can be passed through a fuel reformer to produce hydrogen. The hydrogen is then converted to electricity through a fuel cell.

As another example, while the biogas is described as being burned apart from the sludge and post-distillate solids, in certain embodiments, all of the waste by-products can be burned together to produce steam.

Products/Co-Products

Alcohols

The alcohol produced can be a monohydroxy alcohol, e.g., ethanol, or a polyhydroxy alcohol, e.g., ethylene glycol or glycerin. Examples of alcohols that can be produced include methanol, ethanol, propanol, isopropanol, butanol, e.g., n-, sec- or t-butanol, ethylene glycol, propylene glycol, 1,4-butane diol, glycerin or mixtures of these alcohols.

Each of the alcohols produced by the plant have commercial value as industrial feedstock. For example, ethanol can be used in the manufacture of varnishes and perfume. As another example, methanol can be used as a solvent used as a component in windshield wiper fluid. As still another example, butanol can be used in plasticizers, resins, lacquers, and brake fluids.

Bioethanol produced by the plant is valuable as an ingredient used in the food and beverage industry. For example, the ethanol produced by the plant can be purified to food grade alcohol and used as a primary ingredient in the alcoholic beverages.

Bioethanol produced by the plant also has commercial value as a transportation fuel. The use of ethanol as a transportation fuel can be implemented with relatively little capital investment from spark ignition engine manufacturers and owners (e.g., changes to injection timing, fuel-to-air ratio, and components of the fuel injection system). Many automotive manufacturers currently offer flex-fuel vehicles capable of operation on ethanol/gasoline blends up to 85% ethanol by volume (e.g., standard equipment on a Chevy Tahoe 4×4).

Bioethanol produced by this plant can be used as an engine fuel to improve environmental and economic conditions beyond the location of the plant. For example, ethanol produced by this plant and used as a fuel can reduce greenhouse gas emissions from manmade sources (e.g., transportation sources). As another example, ethanol produced by this plant and used as an engine fuel can also displace consumption of gasoline refined from oil.

Bioethanol has a greater octane number than conventional gasoline and, thus, can be used to improve the performance (e.g., allow for higher compression ratios) of spark ignition engines. For example, small amounts (e.g., 10% by volume) of ethanol can be blended with gasoline to act as an octane enhancer for fuels used in spark ignition engines. As another example, larger amounts (e.g., 85% by volume) of ethanol can be blended with gasoline to further increase the fuel octane number and displace larger volumes of gasoline.

Bioethanol strategies are discussed, e.g., by DiPardo in *Journal of Outlook for Biomass Ethanol Production and Demand (EIA Forecasts)*, 2002; Sheehan in *Biotechnology Progress*, 15:8179, 1999; Martin in *Enzyme Microbes Technology*, 31:274, 2002; Greer in *BioCycle*, 61-65, April 2005; Lynd in *Microbiology and Molecular Biology Reviews*, 66:3, 506-577, 2002; Ljungdahl et al. in U.S. Pat. No. 4,292,406; and Bellamy in U.S. Pat. No. 4,094,742.

Organic Acids

The organic acids produced can include monocarboxylic acids or a polycarboxylic acids. Examples of organic acids include formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids.

Foodstocks

In some embodiments, all or a portion of the fermentation process can be interrupted before the cellulosic material is completely converted to ethanol. The intermediate fermentation products include high concentrations of sugar and carbohydrates. These intermediate fermentation products can be used in preparation of food for human or animal consumption. In some embodiments, irradiation pretreatment of the cellulosic material will render the intermediate fermentation products sterile (e.g., fit for human consumption). In some embodiments, the intermediate fermentation products will require post-processing prior to use as food. For example, a dryer can be used to remove moisture from the intermediate fermentation products to facilitate storage, handling, and shelf-life. Additionally or alternatively, the intermediate fermentation products can be ground to a fine particle size in a stainless-steel laboratory mill to produce a flour-like substance.

Animal Feed

Distillers grains and solubles can be converted into a valuable byproduct of the distillation-dehydration process. After the distillation-dehydration process, distillers grains and solubles can be dried to improve the ability to store and handle the material. The resulting dried distillers grains and solubles (DDGS) is low in starch, high in fat, high in protein, high in fiber, and high in phosphorous. Thus, for example, DDGS can be valuable as a source of animal feed (e.g., as a feed source for dairy cattle). DDGS can be subsequently combined with nutritional additives to meet specific dietary requirements of specific categories of animals (e.g., balancing digestible lysine and phosphorus for swine diets).

Pharmaceuticals

The pretreatment processes discussed above can be applied to plants with medicinal properties. In some embodiments, sonication can stimulate bioactivity and/or bioavailabilty of the medicinal components of plants with medicinal properties. Additionally or alternatively, irradiation stimulates bioactivity and/or bioavailabilty of the medicinal components of plants with medicinal properties. For example, sonication and irradiation can be combined in the pretreatment of willow bark to stimulate the production of salicin.

Nutriceuticals

In some embodiments, intermediate fermentation products (e.g., products that include high concentrations of sugar and carbohydrates) can be supplemented to create a nutriceutical. For example, intermediate fermentation products can be supplemented with calcium create a nutriceutical that provides energy and helps improve or maintain bone strength.

Other embodiments are within the scope of the following claims.

What is claimed is:

1. A method of processing biomass materials using a screw extrusion process, the method comprising:
    conveying biomass material through a screw extruder comprising a co-extruder having a first barrel and a second barrel, wherein the conveying step comprises conveying a first biomass material through the first barrel and conveying a second biomass material through the second barrel;
    applying compression and shear forces via a plurality of interpenetrate helicoidal surfaces within the screw extruder, the forces effective to reduce one or more dimensions of individual pieces of biomass material;
    exposing the biomass material to a plurality of scanning electron beam emitters while conveying the biomass material through the screw extruder, the scanning electron beam emitters each effecting a desired dose of electron beam radiation, wherein the exposing step comprises exposing the first biomass material to a first dose of electron beam irradiation and exposing the second biomass material to a second dose of electron beam irradiation; and producing an extrudate comprising the material discharged from the screw extrusion process.

2. The method of claim 1, wherein the first biomass material differs from the second biomass material prior to introduction to the screw extruder.

3. The method of claim 2, wherein the first biomass material differs from the second biomass material by virtue of one or more of the following characteristics: source of biomass material, type of biomass material, level of recalcitrance, average molecular weight, average crystallinity, surface area, average fiber length, average length-to-diameter ratio, average BET surface area, bulk density, degree of polymerization, porosity, degree of branching, degree of grafting, domain size of the biomass material, and molecular make-up of the biomass material.

4. The method of claim 2, wherein the individual pieces of biomass of the first biomass material have one or more dimensions which, on average, exceed the corresponding one or more dimensions of the individual pieces of biomass of the second biomass material.

5. The method of claim 2, wherein the first dose of electron beam irradiation is greater than the second dose of electron beam irradiation.

6. The method of claim 5, wherein the first dose of electron beam irradiation is at least 100 Mrad and the second dose of electron beam irradiation is at least 10 Mrad.

7. The method of claim 2, wherein the first dose of electron beam irradiation is applied at a first dose rate and the second dose of electron beam irradiation is applied at a second dose rate, the first dose rate differing from the second dose rate.

8. The method of claim 7, wherein the first dose rate is greater than the second dose rate.

9. The method of claim 2, wherein conveying comprises selectively advancing the first biomass material through a plurality of apertures in the first barrel after a desired effect of the first barrel has been attained, and selectively advancing the second biomass material through a plurality of apertures in the second barrel after a desired effect of the second barrel has been attained, the desired effect of the first barrel differing from the desired effect of the second barrel.

10. The method of claim 9, wherein the desired effect of the first barrel and the desired effect of the second barrel each comprises a change in one or more of: level of recalcitrance, average molecular weight, average crystallinity, surface area, average fiber length, average length-to-diameter ratio, average BET surface area, bulk density, degree of polymerization, porosity, degree of branching, degree of grafting, domain size of the biomass material, and molecular make-up of the biomass material.

11. The method of claim 2, wherein the extrudate comprises a multi-layer composite, the composite having a first layer formed from the material discharged from the first barrel and a second layer formed from the material discharged from the second barrel.

12. The method of claim 2, wherein the screw extrusion process comprises one or more of the following elements: a mixing element, a pulverizing element, and a kneading element; and the one or more elements are effective to provide a homogeneous extrudate comprising the material discharged from the first barrel and the material discharged from the second barrel.

13. The method of claim 1, wherein the first biomass material and the second biomass material are derived from the same source.

14. The method of claim 13, wherein the first dose of electron beam irradiation is greater than the second dose of electron beam irradiation.

15. The method of claim 14, wherein the first dose of electron beam irradiation is at least 100 Mrad and the second dose of electron beam irradiation is at least 10 Mrad.

16. The method of claim 13, wherein the first dose of electron beam irradiation is applied at a first dose rate and the second dose of electron beam irradiation is applied at a second dose rate, the first dose rate differing from the second dose rate.

17. The method of claim 16, wherein the first dose rate is greater than the second dose rate.

18. The method of claim 13, wherein conveying comprises selectively advancing the first biomass material through a plurality of apertures in the first barrel after a desired effect of the first barrel has been attained, and selectively advancing the second biomass material through a plurality of apertures in the second barrel after a desired effect of the second barrel has been attained, the desired effect of the first barrel differing from the desired effect of the second barrel.

19. The method of claim 18, wherein the desired effect of the first barrel and the desired effect of the second barrel each comprises a change in one or more of: level of recalcitrance, average molecular weight, average crystallinity, surface area, average fiber length, average length-to-diameter ratio, average BET surface area, bulk density, degree of polymerization, porosity, degree of branching, degree of grafting, domain size of the biomass material, and molecular make-up of the biomass material.

20. The method of claim 13, wherein the extrudate comprises a multi-layer composite, the composite having a first layer formed from the material discharged from the first barrel and a second layer formed from the material discharged from the second barrel.

21. The method of claim 13, wherein the screw extrusion process comprises one or more of the following elements: a mixing element, a pulverizing element, and a kneading element; and the one or more elements are effective to provide a homogeneous extrudate comprising the material discharged from the first barrel and the material discharged from the second barrel.

22. The method of claim 1, wherein the first dose of electron beam irradiation and the second dose of electron beam irradiation are each provided at a dose rate of 1 Mrad per second to about 10 Mrad per second.

23. The method of claim 1, wherein the first dose of electron beam irradiation and the second dose of electron beam irradiation are each between about 10 Mrad and about 150 Mrad.

* * * * *